(12) United States Patent
Galun et al.

(10) Patent No.: US 6,410,009 B1
(45) Date of Patent: *Jun. 25, 2002

(54) PHARMACEUTICAL COMPOSITION FOR TREATING HEPATITIS B VIRUS (HBV) INFECTION

(75) Inventors: Eithan Galun, Har Adar; Orit Nahor, Jerusalem, both of (IL); Hubert E. Blum, Freiburg (DE)

(73) Assignee: Hadasit Medical Research Services & Development Co., Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/439,856

(22) Filed: Nov. 12, 1999

Related U.S. Application Data

(63) Continuation-in-part of application No. 08/795,473, filed on Feb. 11, 1997, now Pat. No. 6,217,858.

(51) Int. Cl.⁷ .................. A61K 45/05; A61K 39/29; A61K 38/20; C07K 4/12; C07K 14/54
(52) U.S. Cl. .................. 424/85.2; 424/85.1; 424/89; 424/225.1; 424/227.1; 424/161.1; 424/185.1; 530/351; 530/300; 514/12; 514/893; 514/894
(58) Field of Search ................. 424/85.1, 189.1, 424/85.2, 89, 161.1, 225.1, 227.1; 514/12, 893, 894; 530/351, 300

(56) References Cited

U.S. PATENT DOCUMENTS

| | | | |
|---|---|---|---|
| 5,158,769 A | 10/1992 | Neurath et al. | ................. 424/89 |
| 5,338,833 A | 8/1994 | Fowlkes et al. | |
| 5,470,952 A | * 11/1995 | Stahl et al. | ................. 530/350 |
| 5,591,827 A | 1/1997 | Brakenhoff et al. | ......... 530/351 |
| 5,919,763 A | 7/1999 | Galun et al. | ................. 514/12 |

FOREIGN PATENT DOCUMENTS

| | | | |
|---|---|---|---|
| EP | 0572118 | 1/1993 | ........... C12P/21/08 |
| FR | 2694767 | 2/1994 | ........... C12P/21/08 |
| WO | WO9210570 | 6/1992 | ........... C12N/15/12 |
| WO | WO9617869 | 6/1996 | ......... C07K/14/715 |
| WO | WO9732891 | 9/1997 | |

OTHER PUBLICATIONS

Pontisso, P., et al., *Virus–Associated Receptor for Polymerized Human Serum Albumin in Acute and in Chronic Hepatitis B Virus Infection* Gastroenterology, vol. 84, No. 2, pp. 220–226 (1983).

Machida, A., et al., *A Hepatitis B Surface Antigen Polypeptide (P31) with the Receptor for Polymerized Human as Well as Chimpanzee Albumins* Gastroenterology, vol. 85, No. 2, pp. 268–274 (1983).

Marie–Louise Michel, et al., *Synthesis in Animal Cells of Hepatitis B Surface Antigen Particles Carrying A Receptor for Polymerized Human Serum, Albumin* Biochemistry, Dec., vol. 81, pp. 7708–7712 (1984).

Machida, A., et al., *A Polypeptide Containing 55 Amino Acid Residues Coded by the pre–S Region of Hepatitis B Virus Deoxyribonucleic Acid Bears the Receptor for Polymerized Human as Well as Chimpanzee Albumins*, Gastroenterology, vol. 86, No. 5, pp. 910–918 (1984).

Pontisso, P., et al., *Human Liver Plasma Membranes Contain Receptors for the Hepatitis B Virus Pre–S1 Region and, via Polymerized Human Serum Albumin, for the Pre–S2 Region*, Journal of Virology, pp. 1981–1988 (1989).

Neurath, A.R., et al., *Identification and Chemical Synthesis of a Host Cell Receptor Binding Site on Hepatitis B Virus*, Cell, vol. 46, pp. 429–436 (1986).

Petit, M.–A., et al., *A Monoclonal Antibody Specific for the Hepatocyte Receptor Binding Site on Hepatitis B Virus*, Molecular Immunology, vol. 26, No. 6, pp. 531–537 (1989).

Neurath, A.R., et al., *Detection of Receptors for Hepatitis B Virus on Cells of Extrahepatic Origin*, Virology, vol. 176, pp. 448–457 (1990).

D'Mello, F., et al., *Definition of the primary Structure of Hepatitis B Virus (HBV) pre–S Hepatocyte Binding Domain Using Random Peptide Libraries* Virology, vol. 237, pp. 319–326 (1997).

Peeples, M. E., et al., *A Cultured Cell Receptor for the Small S Protein of Hepatitis B Virus* Virology vol. 160, pp. 135–142 (1987).

Komai, K., et al., *Physiology and Function of the Vero Cell Receptor for the Hepatitis B Virus Small S Protein*, Virology vol. 177, pp. 332–338 (1990).

Komai, K., et al., *The Vero Cell Receptor for the Hepatitis B Virus Small S Protein Is a Sialoglycoprotein* Virology vol. 163, pp. 629–634 (1988).

Pontisso, P., et al., *The preS1 Domain of Hepatitis B Virus and IgA Cross–React in Their Binding to the Hepatocyte Surface*, Journal of General Virology vol. 73, pp. 2041–2045 (1992).

(List continued on next page.)

*Primary Examiner*—Ali R. Salimi
*Assistant Examiner*—Bao Qun Li
(74) *Attorney, Agent, or Firm*—Davidson, Davidson & Kappel, LLC

(57) ABSTRACT

The invention provides a pharmaceutical composition for the treatment of hepatitis B virus (HBV) infection, comprising an amount of a soluble active agent which interacts with at least one of the binding sites between hIL6 and pS1 and between hIL6 and hepatocytes and other HBV-permissive cells, the active agent being present in sufficient amount to competitively bind to at least one of the sites and thereby to prevent hIL6-mediated HBV infection of hepatocytes and other HBV-permissive cells.

21 Claims, 17 Drawing Sheets

(3 of 17 Drawing Sheet(s) Filed in Color)

OTHER PUBLICATIONS

Dash, S., et al., *Significance of Natural Polymerized Albumin and its Receptor in Hepatitis B Infection of Hepatocytes*, Hepatology vol. 13, No. 1, pp. 134–142 (1991).

Romet–Lemonne, J., et al., Science vol. 221, pp. 667–669 (1983).

Budkowska, A., et al., *Hepatitis B Virus (HBV) Binding Factor in Human Serum: Candidate for a Soluble form of Hepatocyte HBV Receptor*, Journal of Virology, vol. 67, No. 7, pp. 4316–4322 (1993).

Gagliardi, M.–C., et al., *Soluble Transferrin mediates Targeting of Hepatitis B Envelope Antigen to Transferrin Receptor and its presentation by Activated T Cells*, Eur. J. Immunol., vol. 24, pp. 1372–1376 (1994).

Treichel, U., et al., *The Asialoglycoprotein Receptor Mediates Hepatic Binding and Upate of Natural Hepatitis B Virus Particles Derived from Viraemic Carriers*, Journal of General Virology, vol. 75, pp. 3021–3029 (1994).

Hertogs, K., et al., *Endonexin II, Present on Human Liver Plasma Membranes, Is a Specific Binding Protein of Small Hepatitis B Virus (HBV) Envelope Protein*, Virology, vol. 197, pp. 549–557 (1993).

Mehdi, H., et al., *Hepatitis B Virus Surface Antigen Binds to Apolipoprotein H*, Journal of Virology, vol. 68, No. 4, pp. 2415–2424 (1994).

Petit, M.–A., et al., *PreS1–Specific Binding proteins as Potential Receptors for Hepatitis B Virus*, Virology, vol. 187, pp. 211–222 (1992).

Franco, A., et al., *Transferrin Receptor Mediates Uptake and presentation of hepatitis B Envelope Antigen by T Lymphocytes*, J. Exp. Med. vol. 175, pp. 1195–1205 (1992).

Dash, S., et al., *Receptor for Pre–S1(21–47) Component of Hepatitis B Virus on the Liver Cell: Role in Virus Cell Interaction*, Journal of Medical Virology, vol. 37, pp. 116–121 (1992).

Mizutani, Y., et al., *Sensitization of Human Renal Cell Carcinoma Cells to cis–Diamminedichloroplatinum (II) by Anti–Interleukin 6 Monoclonal Antibody or Anti–Interleukin 6 Receptor Monoclonal Antibody*, Cancer Research, vol. 55, pp. 590–596 (1995).

Martin, F., et al., *The Affinity–Selection of a Minibody Polypeptide Inhibitor of Human Interleukin–6*, The EMBO Journal, vol. 13, No. 22, pp. 5303–5309 (1994).

Peters, M., et al., *The Function of the Soluble Interleukin 6 (IL–6) Receptor In Vivo: Sensitization of Human Soluble IL–6 Receptor Transgenic Mice Towards IL–6*, J. Exp. Med., vol. 183, pp. 1399–1406 (1996).

Peters, M., et al., *The Function of the Soluble IL–6 Receptor in Vivo*, Immunology Letters, vol. 54, pp. 177–184 (1996).

Sporeno, E., et al., *Human Interleukin–6 Receptor Super–Antagonists with High Potency and Wide Spectrum on Multiple Myeloma Cells*, Blood, vol. 87, No. 11, pp. 4510–4519 (1996).

Masood, R., et al., *Inhibition of Aids–Associated Kaposi's Sarcoma Cell Growth*, Aids Research and Human Retroviruses, vol. 10, pp. 969–970 (1994) (Abstract).

Brakenhoff, J.P.J., et al., *Development of a Human Interleukin–6 Receptor Antagonist*, The Journal of Biological Chemistry, vol. 269, No. 1, pp. 86–93 (1994).

Somers, W., et al., *1.9 A crystal Structure of Interleukin 6: Implications for a Novel Mode of Receptor Dimerization and Signaling*, The EMBO Journal, vol. 16, No. 5, pp. 989–997 (1997).

Nishimura, et al., *Folding Topologies of Human Interleukin–6 and its Mutants as Studied by NMR Spectroscopy*, Biochemistry 35:273–281 (1996). MEDLINE 96134845, Abstract.

Hibi, etal., *Molecular Cloning and Expression of an IL–6 Signal Transducer, gp 130.*, Cell 63(6):1149–1157 (1990). MEDLINE 91084844, Abstract.

May, et al., *Anti–beta–interferon Antibodies Inhibit the Increased Expression of HLA–B7 mRNA in Tumore Necrosis Factor–Treated Human Fibroblasts: Structural Studies of the Beta 2 Interferon Involved.*, Proc. Nat'l Acad. Sci. U.S.A. vol. 83, No. 23, 8957–8961 (1986). MEDLINE 87067433, Abstract.

Schooltink, et al., *Structural and Functional Studies on the Human Hepatic Interleukin–6 Receptor. Molecular Cloning and Overexpression in HepG2 cells.*, Biochem. J. 277:659–664, 1991, MEDLINE 91336983, Abstract.

Yamasaki, et al., *Cloning and Expression of the Human Interleukin–6, (BSF–2/IFN beta 2) Receptor*, Science vol. 241 pp. 825–828 (1988). MEDLINE 88305347, Abstract.

Neurath, A. R., et al., *Search for Hepatitis B Virus Cell Receptors Reveals Binding Sites for Interleukin 6 on the Virus Envelope Protein*, J. Exp. Med., vol. 175 pp. 461–469 (1992).

Savino, R., et al., *Generation of Interleukin–6 Receptor Antagonists by Molecular–Modeling Guided Mutagenesis of Residues Important for gp 130 Activation*, The EMBO Journal, vol. 13, No. 6, pp. 1357–1367 (1994).

Neurath, R., et al., *Cells Transfected with Human Interleukin 6 cDNA Acquire Binding Sites for the Hepatitis B Virus Envelope Protein*, J. Exp. Med., vol. 176, pp. 1561–1569 (1992).

Lentz, T.L., *The Recognition Event Between Virus and Host Cell Receptor: a Target for Antiviral Agents*, Journal of General Virology, 71, pp. 751–766. Review Article (1990).

Niepmann, et al., *A Short Cis–acting Sequence is Required for Hepatitis B Virus Pregenome Encapsidation and Sufficient for Packaging of Foreign RNA*, The EMBO Journal vol. 9, No., 10 pp. 3389–3396 (1990).

Knaus, T., et al., *The Encapsidation Signal on the Hepatitis B virus RNA Pregenome Forms a Stem–loop Structure that is Critical for its Function, Nucleic Acids Research*, vol. 21, No. 17 pp. 3967–3975 (1993).

Blum, H. E., et al., *Naturally Occurring Missense Mutation in the Polymerase Gene Terminating Hepatitis B Virus Replication*, Journal of Virology, vol. 65, No. 4, pp. 1836–1842 (1991).

Perales, et al., *Gene Transfer in vivo: Sustained Expression and Regulation of Genes Introduced into the Liver by Receptor–Targeted Uptake*, Proc. Natl. Acad. Sci. USA, vol. 91, pp. 4086–4090 (1994).

Neurath, et al., *Antibodies to Synthetic Peptides from the preS1 Region of the Hepatitis B virus (HBV) Envelope (env) Protein are Virus–neutralizing and Protective*, Vaccine vol. 7, pp. 234–236 (1989).

Koishihara et al., *Preparation of Peptide Human B–Cell Stimulating Factor 2 (BSF2)*, Jul. 24, 1990, Antagonists, Abstract of Japanese Patent No. 02188600.

Macri P., et al., *Delayed Morbidity and Mortality of Albumins/SV40 T–Antigen Transgenic Mice after Insertion of an α–Feto–protein/Herpes Virus Thymidine Kinase Transgene and Treatment with Ganciclovir*, Human Gene Therapy 5:175–182 (1994). Abstr.

Baroja, M. L., et al., *T cell hyperreactivity ti IL–6 in chronic nonviremic HBV carriers despite normal IL–6 receptor or gp130 expression*, Viral Immunol, vol. 9, No. 3, pp. 187–194 (1996). Abstract.

Fischer, M., et al., A bioactive designer cytokine for human hematopoietic progenitor cell expansion, Nature Biotechnol. vol. 15, pp. 142–145 ( 1997).

De Hon, F.D., et al., Development of an Interleukin (IL) 6 Receptor antoganoist that inhibits IL–6–dependent growth of human myeloma cells, J. Exp. Med. vol. 180, pp. 2395–2400 (1994).

Taga, T., et al., GP130 and the Interleukin–6 Family of Cytokines, Ann. Rev. Immunol. vol. 15, pp. 797–819 (1997).

Rakemann et al., *The Designer Cytokine Hyper–Interleukin–6 is a Potent Activator of STAT3–dependent Gene Tanscription in Vivo and in Vitro*, J. Biol. Chem. vol. 274, pp. 1257–1266 (1999).

Schirmacher, et al., *Hepatocellular Hyperplasia, Plasmacytoma Formation, and Extramedullary Hematopoiesis in Interleukin(IL)–6/Soluble IL–6 Receptor Double–Transgenic Mice*, Am. J. Pathol. vol. 153, pp. 639–648 (1988).

Galun, et al., *Hepatitis C Virus Viremia in SCID—BNX Mouse Chimera*, J. Infectious Disease vol. 175, pp. 25–30 (1995).

Lubin, et al., *Engraftment and Development of Human T and B Cells in Mice After Bone Marrow Transplatation*, Science vol. 252, pp. 427–431 (1991).

Galun, E., et al., *Hepatitis B Virus Infection Associated with Hematopoietic Tumors*, Amer. J. Pathol. vol. 145, pp. 1001–1007 (1994).

Galun, E., et al., *Human Non–hepatocytes Support Hepadnaviral Replication and Virion Production*, J. Gen. Virol. vol. 73, pp. 173–178 (1992).

Mackiewicz, A. et al., *Complex of Soluble Human IL–6–Receptor/IL–6 Up–Regulates Expression of Acute–Phase Proteins*, J. Immunol. vol. 149, pp. 2021–2027 (1992).

Bauer, J., et al., *Regulation of Interleukin–6 Receptor Expression in Human Monocytes and Hepatocytes*, FEBS Lett. vol. 249, pp. 27–30 (1989).

Ehlers, M., et al., *Identification of Two Novel Regions of Human, IL–6 Responsible for Receptor Binding and Signal Transduction*, J. Immunol. vol. 153, p. 1744 (1994).

Dittrich, E., et al., *Identification of a Region within the Cytoplasmic Domain of the Interleukin–6 (IL–6) Signal Transducer gp130 Important for Ligand–induced Endocytosis of the IL–6 Receptor*, J. Biol. Chem. vol. 269, pp. 1–914–19020 (1994).

Korba, B.E., et al., *Hepadnavirus Infection of Peripheral Blood Lymphocytes in Vivo: Woodchuck and Chimpanzee Models of Viral Hepatitis*, J. Virol. vol. 58, pp. 1–8 (1986).

Laskus, T., et al., *Detection and Sequence Analysis of Hepatitis B Virus Integration in Peripheral Blood Mononuclear Cells*, J. Virol. vol. 73, pp. 1235–1238 (1997).

Laskus, T., et al., *Comparison of Hepatitis B Virus Core Promoter Sequences in Peripheral Blood Mononuclear Cells and Serum from Patients with Hepatitis B*, J. Gen. Virol. Vol. 78, pp. 649–653 (1997).

Peters, M., et al., *Interleukin–6 and Soluble Interleukin–6 Receptor: Direct Stimulation of gp130 and Hematopoiesis*, Blood vol. 92, pp. 3495–3504 (1998).

Klein, et al., *Comparison of Methods for Extraction of Nucleic Acid from Hemolytic Serum for PCR Amplification of Hepatitis B Virus DNA Sequences*, J. Clin. Microb. vol. 35, pp. 1897–1899 (1977).

Galun, E., et al., *Liver Regeneration Induced by a Designer Human IL–6/sIL–6R Fusion Protein Reverses Severe Hepatocellular Injury*, FASEB J. Vol. 14, pp. 1979–1987 (2000).

Betz, U.A.K.., Postnatally Induced Inactivation of gp 130 in Mice Results in Neurological, Cardiac, Hematopoietic, Immunological, Hepatic, and Pulmonary Defects, J. Exp. Med. vol. 10, No. 10, pp. 1955–1965 (1998).

Blum, H., et al., *Detection of Hepatitis B Virus DNA in Hepatocytes, Bile Duct Epithelium, and Vascular Elements by in Situ Hybridization*, Proc. Natl. Acad. Sci. U.S.A. vol. 80, pp. 6685–6688 (1983).

Kishimoto, T., et al., *Interleukin–6 and its Receptor: A Paradigm for Cytokines*, Science vol. 258, p. 593 (1992).

Rose–John, S. et al., *Intracellular Retention of interleukin–6 Abrogates Signaling*, J. Biol. Chem. vol. 268, pp. 22084–22091 (1993).

\* cited by examiner

FIG. 5

| | | | | | |
|---|---|---|---|---|---|
| ATTCTGCCCT | CGAGCCCACC | GGGAACGAAA | GAGAAGCTCT | ATCTCCCCTC | 50 |
| CAGGAGCCCA | GCTATGAACT | CCTTCTCCAC | AAGCGCCTTC | GGTCCAGTTG | 100 |
| CCTTCTCCCT | GGGGCTGCTC | CTGGTGTTGC | CTGCTGCCTT | CCCTGCCCCA | 150 |
| GTACCCCCAG | GAGAAGATTC | CAAAGATGTA | GCCGCCCCAC | ACAGACAGCC | 200 |
| ACTCACCTCT | TCAGAACGAA | TTGACAAACA | AATTCGGTAC | ATCCTCGACG | 250 |
| GCATCTCAGC | CCTGAGAAAG | GAGACATGTA | ACAAGAGTAA | CATGTGTGAA | 300 |
| AGCAGCAAAG | AGGCACTGGC | AGAAAACAAC | CTGAACCTTC | CAAAGATGGC | 350 |
| TGAAAAGAT | GGATGCTTCC | AATCTGGATT | CAATGAGGAG | ACTTGCCTGG | 400 |
| TGAAAATCAT | CACTGGTCTT | TTGGAGTTTG | AGGTATACCT | AGAGTACCTC | 450 |
| CAGAACAGAT | TTGAGAGTAG | TGAGGAACAA | GCCAGAGCTG | TCCAGATGAG | 500 |
| TACAAAAGTC | CTGATCCAGT | TCCTGCAGAA | AAAGGCAAAG | AATCTAGATG | 550 |
| CAATAACCAC | CCCTGACCCA | ACCACAAATG | CCAGCCTGCT | GACGAAGCTG | 600 |
| CAGGCACAGA | ACCAGTGGCT | GCAGGACATG | ACAACTCATC | TCATTCTGCG | 650 |
| CAGCTTTAAG | GAGTTCCTGC | AGTCCAGCCT | GAGGGCTCTT | CGGCAAATGT | 700 |
| AGCATGGGCA | CCTCAGATTG | TTGTTGTTAA | TGGGCATTCC | TTCTTCTGGT | 750 |
| CAGAAACCTG | TCCACTGGGC | ACAGAACTTA | TGTTGTTCTC | TATGGAGAAC | 800 |
| TAAAAGTATG | AGCGTTAGGA | CACTATTTTA | ATTATTTTA | ATTTATTAAT | 850 |
| ATTTAAATAT | GTGAAGCTGA | GTTAATTTAT | GTAAGTCATA | TTTTATATTT | 900 |
| TTAAGAAGTA | CCACTTGAAA | CATTTTATGT | ATTAGTTTTG | AAATAATAAT | 950 |
| GGAAAGTGGC | TATGCAGTTT | GAATATCCTT | TGTTTCAGAG | CCAGATCATT | 1000 |
| TCTTGGAAAG | TGTAGGCTTA | CCTCAAATAA | ATGGCTAACT | TTATACATAT | 1050 |
| TTTTAAAGAA | ATATTTATAT | TGTATTTATA | TAATGTATAA | ATGGTTTTTA | 1100 |
| TACCAATAAA | TGGCATTTTA | AAAAATTC | | | 1128 |

FIG. 6a

| | | | | | |
|---|---|---|---|---|---|
| GGGGTCCCC | TGTTCTCCCC | GCTCAGGTGC | GGCGCTGTGG | CAGGAAGCCA | 50 |
| CCCCCTCGT | CGGCCGGTGC | GCGGGGCTGT | TGCGCCATCC | GCTCCGGCTT | 100 |
| TCGTAACCGC | ACCCTGGGAC | GGCCCAGAGA | CGCTCCAGCG | CGAGTTCCTC | 150 |
| AAATGTTTC | CTGCGTTGCC | AGGACCGTCC | GCCGCTCTGA | GTCATGTGCG | 200 |
| AGTGGGAAGT | CGCACTGACA | CTGAGCCGGG | CCAGAGGGAG | AGGAGCCGAG | 250 |
| CGCGGGCGG | GGCCGAGGGA | CTCGCAGTGT | GTGTAGAGAG | CCGGGCTCCT | 300 |
| GCGGATGGGG | GCTGCCCCG | GGGCCTGAGC | CCGCCTGCCC | GCCCACCGCC | 350 |
| CCGCCCCGCC | CCTGCCACCC | CTGCCGCCCG | GTTCCCATTA | GCCTGTCCGC | 400 |
| CTCTGCGGGA | CCATGGAGTG | GTAGCCGAGG | AGGAAGCATG | CTGGCCGTCG | 450 |
| GCTGCGCGCT | GCTGGCTGCC | CTGCTGGCCG | CGCCGGGAGC | GGCGCTGGCC | 500 |
| CCAAGGCGCT | GCCCTGCGCA | GGAGGTGGCA | AGAGGCGTGC | TGACCAGTCT | 550 |
| GCCAGGAGAC | AGCGTGACTC | TGACCTGCCC | GGGGTAGAG | CCGGAAGACA | 600 |

FIG.6b

| | | | | | 650 |
|---|---|---|---|---|---|
| ATGCCACTGT | TCACTGGGTG | CTCAGGAAGC | CGGCTGCAGG | CTCCCACCCC | 650 |
| AGCAGATGGG | CTGGCATGGG | AAGGAGGCTG | CTGCTGAGGT | CGGTGCAGCT | 700 |
| CCACGACTCT | GGAAACTATT | CATGCTACCG | GGCCGGCCGC | CCAGCTGGGA | 750 |
| CTGTGCACTT | GCTGGTGGAT | GTCCCCCCG | AGGAGCCCCA | GCTCTCCTGC | 800 |
| TTCCGGAAGA | GCCCCCTCAG | CAATGTTGTT | TGTGAGTGGG | GTCCTCGGAG | 850 |
| CACCCCATCC | CTGACGACAA | AGGCTGTGCT | CTTGGTGAGG | AAGTTTCAGA | 900 |
| ACAGTCCGGC | CGAAGACTTC | CAGGAGCCGT | GCCAGTATTC | CCAGGAGTCC | 950 |
| CAGAAGTCT | CCTGCCAGTT | AGCAGTCCCG | GAGGGAGACA | GCTCTTTCTA | 1000 |
| CATAGTGTCC | ATGTGCGTCG | CCAGTAGTGT | CGGGAGCAAG | TTCAGCAAAA | 1050 |
| CTCAAACCTT | TCAGGGTTGT | GGAATCTTGC | AGCCTGATCC | GCCTGCCAAC | 1100 |
| ATCACAGTCA | CTGCCGTGGC | CAGAAACCCC | CGCTGGCTCA | GTGTCACCTG | 1150 |
| GCAAGACCCC | CACTCCTGGA | ACTCATCTTT | CTACAGACTA | CGGTTTGAGC | 1200 |

FIG.6c

| | | | | |
|---|---|---|---|---|
| TCAGATATCG | GGCTGAACGG | TCAAAGACAT | TCACAACATG | GATGGTCAAG | 1250
| GACCTCCAGC | ATCACTGTGT | CATCCACGAC | GCCTGGAGCG | GCCTGAGGCA | 1300
| CGTGGTGCAG | CTCGTGCCC | AGGAGGAGTT | CGGGCAAGGC | GAGTGGAGCG | 1350
| AGTGGAGCCC | GGAGGCCATG | GGCACGCCTT | GGACAGAATC | CAGGAGTCCT | 1400
| CCAGCTGAGA | ACGAGGTGTC | CACCCCCATG | CAGGCACTTA | CTACTAATAA | 1450
| AGACGATGAT | AATATTCTCT | TCAGAGATTC | TGCAAATGCG | ACAAGCCTCC | 1500
| CAGTGCAAGA | TTCTCTTCA | GTACCACTGC | CCACATTCCT | GGTTGCTGGA | 1550
| GGGAGCCTGG | CCTTCGGAAC | GCTCCCTCTGC | ATTGCCATTG | TTCTGAGGTT | 1600
| CAAGAAGACG | TGGAAGCTGC | GGGCTCTGAA | GGAAGGCAAG | ACAAGCATGC | 1650
| ATCCGCCGTA | CTCTTTGGGG | CAGCTGGTCC | CGGAGAGGCC | TCGACCCACC | 1700
| CCAGTGCTTG | TTCCTCTCAT | CTCCCCACCG | GTGTCCCCCA | GCAGCCTGGG | 1750

FIG. 6d

| | | | | | |
|---|---|---|---|---|---|
| GTCTGACAAT | ACCTCGAGCC | ACAACCGACC | AGATGCCAGG | GACCCACGGA | 1800 |
| GCCCTTATGA | CATCAGCAAT | ACAGACTACT | TCTTCCCCAG | ATAGCTGGCT | 1850 |
| GGGTGGCACC | AGCAGCCTGG | ACCCTGTGGA | TGACAAAACA | CAAACGGGCT | 1900 |
| CAGCAAAAGA | TGCTTCTCAC | TGCCATGCCA | GCTTATCTCA | GGGGTGTGCG | 1950 |
| GCCTTTGGCT | TCACGGAAGA | GCCTTGCGGA | AGGTTCTACG | CCAGGGGAAA | 2000 |
| ATCAGCCTGC | TCCAGCTGTT | CAGCTGGTTG | AGGTTTCAAA | CCTCCCTTTC | 2050 |
| CAAATGCCCA | GCTTAAAGGG | GTTAGAGTGA | ACTTGGGCCA | CTGTGAAGAG | 2100 |
| AACCATATCA | AGACTCTTTG | GACACTCACA | CGGACACTCA | AAAGCTGGGC | 2150 |
| AGGTTGGTGG | GGGCCTCGGT | GTGGAGAAGC | GGCTGGCAGC | CCACCCCTCA | 2200 |
| ACACCTCTGC | ACAAGCTGCA | CCCTCAGGCA | GGTGGGATGG | ATTTCCAGCC | 2250 |
| AAAGCCTCCT | CCAGCCGCCA | TGCTCCTGGC | CCACTGCATC | GTTTCATCTT | 2300 |
| CCAACTCAAA | CTCTTAAAAC | CCAAGTGCCC | TTAGCAAATT | CTGTTTTTCT | 2350 |
| AGGCCTGGGG | ACGGCTTTTA | CTTAAACGCC | AAGGCCTGGG | GGAAGAAGCT | 2400 |
| CTCTCCTCCC | TTTCTTCCCT | ACAGTTCAAA | AACAGCTGAG | GGTGAGTGGG | 2450 |
| TGAATAATAC | AGTATGTCAG | GGCCTGGTCG | TTTTCAACAG | AATTATAATT | 2500 |
| AGTTCCTCAT | TAGCAGTTTT | GCCTAAATGT | GAATGATGAT | CCTAGGCATT | 2550 |
| TGCTGAATAC | AGAGGCAACT | GCATTGGCTT | TGGGTTGCAG | GACCTCAGGT | 2600 |
| GAGAAGCAGA | GGAAGGAGAG | GAGAGGGGCA | CAGGGTCTCT | ACCATCCCCT | 2650 |
| GTAGAGTGGG | AGCTGAGTGG | GGGATCACAG | CCTCTGAAAA | CCAATGTTCT | 2700 |
| CTCTTCTCCA | CCTCCCACAA | AGGAGAGCTA | GCAGCAGGGA | GGGCTTCTGC | 2750 |
| CATTTCTGAG | ATCAAAACGG | TTTTACTGCA | GCTTTGTTTG | TTGTCAGCTG | 2800 |
| AACCTGGGTA | ACTAGGGAAG | ATAATATTAA | GGAAGACAAT | GTGAAAAGAA | 2850 |
| AAATGAGCCT | GGCAAGAATG | CGTTTAAACT | TGGTTTTTAA | AAAACTGCTG | 2900 |
| ACTGTTTTCT | CTTGAGAGGG | TGGAATATCC | AATATTCGCT | GTGTCAGCAT | 2950 |
| AGAAGTAACT | TACTTAGGTG | TGGGGGAAGC | ACCATAACTT | TGTTTAGCCC | 3000 |
| AAAACCAAGT | CAAGTGAAAA | AGGAGGAAGA | GAAAAAATAT | TTTCCTGCCA | 3050 |
| GGCATGGAGG | CCCACGCACT | TCGGGAGGTC | GAGGCAGGAG | GATCACTTGA | 3100 |
| GTCCAGAAGT | TTGAGATCAG | CCTGGGCAAT | GTGATAAAAC | CCCATCTCTA | 3150 |
| CAAAAAGCAT | AAAAATTAGC | CAAGTGTGGT | AGAGTGTGCC | TGAAGTCCCA | 3200 |
| GATACTTGGG | GGGCTGAGGT | GGGAGGATCT | CTTGAGCCTG | GGAGGTCAAG | 3250 |
| GCTGCAGTGA | GCCGAGATTG | CACCACTGCA | CTCCAGCCTG | GGGTGACAGA | 3300 |
| GCAAGTGAGA | CCCTGTCTC | | | | 3319 |

FIG. 7

| | | | | | |
|---|---|---|---|---|---|
| ATTAGCCTGT | CCGCCTCTGC | GGGACCATGG | AGTGGTAGCC | GAGGAGGAAG | 50 |
| CATGCTGGCC | GTCGGCTGCG | CGCTGCTGGC | TGCCCTGCTG | GCCGCGCCGG | 100 |
| GAGCGGCGCT | GGCCCCAAGG | CGCTGCCCTG | CGCAGGAGGT | GGCGAGAGGC | 150 |
| GTGCTGACCA | GTCTGCCAGG | AGACAGCGTG | ACTCTGACCT | GCCCGGGGGT | 200 |
| AGAGCCGGAA | GACAATGCCA | CTGTTCACTG | GGTGCTCAGG | AAGCCGGCTG | 250 |
| CAGGCTCCCA | CCCCAGCAGA | TGGGCTGGCA | TGGGAAGGAG | GCTGCTGCTG | 300 |
| AGGTCGGTGC | AGCTCCACGA | CTCTGGAAAC | TATTCATGCT | ACCGGGCCGG | 350 |
| CCGCCCAGCT | GGGACTGTGC | ACTTGCTGGT | GGATGTTCCC | CCCGAGGAGC | 400 |
| CCCAGCTCTC | CTGCTTCCGG | AAGAGCCCCC | TCAGCAATGT | TGTTTGTGAG | 450 |
| TGGGGTCCTC | GGAGCACCCC | ATCCCTGACG | ACAAAGGCTG | TGCTCTTGGT | 500 |
| GAGGAAGTTT | CAGAACAGTC | CGGCCGAAGA | CTTCCAGGAG | CCGTGCCAGT | 550 |
| ATTCCCAGGA | GTCCCAGAAG | TTCTCCTGCC | AGTTAGCAGT | CCCGGAGGGA | 600 |
| GACAGCTCTT | TCTACATAGT | GTCCATGTGC | GTCGCCAGTA | GTGTCGGGAG | 650 |
| CAAGTTCAGC | AAAACTCAAA | CCTTTCAGGG | TTGTGGAATC | TTGCAGCCTG | 700 |
| ATCCGCCTGC | CAACATCACA | GTCACTGCCG | TGGCCAGAAA | CCCCCGCTGG | 750 |
| CTCAGTGTCA | CCTGGCAAGA | CCCCCACTCC | TGGAACTCAT | CTTTCTACAG | 800 |
| ACTACGGTTT | GAGCTCAGAT | ATCGGGCTGA | ACGGTCAAAG | ACATTCACAA | 850 |
| CATGGATGGT | CAAGGACCTC | CAGCATCACT | GTGTCATCCA | CGACGCCTGG | 900 |
| AGCGGCCTGA | GGCACGTGGT | GCAGCTTCGT | GCCCAGGAGG | AGTTCGGGCA | 950 |
| AGGCGAGTGG | AGCGAGTGGA | GCCCGGAGGC | CATGGGCACG | CCTTGGACAG | 1000 |
| AATCCAGGAG | TCCTCCAGCT | GAGAACGAGG | TGTCCACCCC | CATGCAGGCA | 1050 |
| CTTACTACTA | ATAAAGACGA | TGATAATATT | CTCTTCAGAG | ATTCTGCAAA | 1100 |
| TGCGACAAGC | CTCCCAGTGC | AAGATTCTTC | TTCAGTACCA | CTGCCCACAT | 1150 |
| TCCTGGTTGC | TGGAGGGAGC | CTGGCCTTCG | GAACGCTCCT | CTGCATTGCC | 1200 |
| ATTGTTCTGA | GGTTCAAGAA | GACGTGGAAG | CTGCGGGCTC | TGAAGGAAGG | 1250 |
| CAAGACAAGC | ATGCATCCGC | CGTACTCTTT | GGGGCAGCTG | GTCCCGGAGA | 1300 |
| GGCCTCGACC | CACCCCAGTG | CTTGTTCCTC | TCATCTCCCC | ACCGGTGTCC | 1350 |
| CCCAGCAGCC | TGGGGTCTGA | CAATACCTCG | AGCCACAACC | GACCAGATGC | 1400 |
| CAGGGACCCA | CGGAGCCCTT | ATGACATCAG | CAATACAGAC | TACTTCTTCC | 1450 |
| CCAGATAGCT | GGCTGGGTGG | CACCAGCAGC | CTGGAC | | 1486 |

FIG. 8a

| | | | | | |
|---|---|---|---|---|---|
| GAGCAGCCAA | AAGGCCCGCG | GAGTCGCGCT | GGGCCGCCCC | GGCGCAGCTG | 50 |
| AACCGGGGGC | CGCGCCTGCC | AGGCCGACGG | GTCTGGCCCA | GCCTGGCGCC | 100 |
| AAGGGGTTCG | TGCGCTGTGG | AGACGCGGAG | GGTCGAGGCG | GCGCGGCCTG | 150 |
| AGTGAAACCC | AATGGAAAAA | GCATGACATT | TAGAAGTAGA | AGACTTAGCT | 200 |
| TCAAATCCCT | ACTCCTTCAC | TTACTAATTT | TGTGATTTGG | AAATATCCGC | 250 |
| GCAAGATGTT | GACGTTGCAG | ACTTGGGTAG | TGCAAGCCTT | GTTTATTTTC | 300 |
| CTCACCACTG | AATCTACAGG | TGAACTTCTA | GATCCATGTG | GTTATATCAG | 350 |
| TCCTGAATCT | CCAGTTGTAC | AACTTCATTC | TAATTTCACT | GCAGTTTGTG | 400 |
| TGCTAAAGGA | AAAATGTATG | GATTATTTTC | ATGTAAATGC | TAATTACATT | 450 |
| GTCTGGAAAA | CAAACCATTT | TACTATTCCT | AAGGAGCAAT | ATACTATCAT | 500 |
| AAACAGAACA | GCATCCAGTG | TCACCTTTAC | AGATATAGCT | TCATTAAATA | 550 |
| TTCAGCTCAC | TTGCAACATT | CTTACATTCG | GACAGCTTGA | ACAGAATGTT | 600 |
| TATGGAATCA | CAATAATTTC | AGGCTTGCCT | CCAGAAAAAC | CTAAAAATTT | 650 |
| GAGTTGCATT | GTGAACGAGG | GGAAGAAAAT | GAGGTGTGAG | TGGGATGGTG | 700 |
| GAAGGGAAAC | ACACTTGGAG | ACAAACTTCA | CTTTAAAATC | TGAATGGGCA | 750 |
| ACACACAAGT | TTGCTGATTG | CAAAGCAAAA | CGTGACACCC | CCACCTCATG | 800 |
| CACTGTTGAT | TATTCTACTG | TGTATTTTGT | CAACATTGAA | GTCTGGGTAG | 850 |
| AAGCAGAGAA | TGCCCTTGGG | AAGGTTACAT | CAGATCATAT | CAATTTTGAT | 900 |
| CCTGTATATA | AAGTGAAGCC | CAATCCGCCA | CATAATTTAT | CAGTGATCAA | 950 |
| CTCAGAGGAA | CTGTCTAGTA | TCTTAAAATT | GACATGGACC | AACCCAAGTA | 1000 |
| TTAAGAGTGT | TATAATACTA | AAATATAACA | TTCAATATAG | GACCAAAGAT | 1050 |
| GCCTCAACTT | GGAGCCAGAT | TCCTCCTGAA | GACACAGCAT | CCACCCGATC | 1100 |
| TTCATTCACT | GTCCAAGACC | TTAAACCTTT | TACAGAATAT | GTGTTTAGGA | 1150 |
| TTCGCTGTAT | GAAGGAAGAT | GGTAAGGGAT | ACTGGAGTGA | CTGGAGTGAA | 1200 |
| GAAGCAAGTG | GGATCACCTA | TGAAGATAGA | CCATCTAAAG | CACCAAGTTT | 1250 |
| CTGGTATAAA | ATAGATCCAT | CCCATACTCA | AGGCTACAGA | ACTGTACAAC | 1300 |
| TCGTGTGGAA | GACATTGCCT | CCTTTTGAAG | CCAATGGAAA | AATCTTGGAT | 1350 |
| TATGAAGTGA | CTCTCACAAG | ATGGAAATCA | CATTTACAAA | ATTACACAGT | 1400 |
| TAATGCCACA | AAACTGACAG | TAAATCTCAC | AAATGATCGC | TATCTAGCAA | 1450 |
| CCCTAACAGT | AAGAAATCTT | GTTGGCAAAT | CAGATGCAGC | TGTTTTAACT | 1500 |
| ATCCCTGCCT | GTGACTTTCA | AGCTACTCAC | CCTGTAATGG | ATCTTAAAGC | 1550 |
| ATTCCCCAAA | GATAACATGC | TTTGGGTGGA | ATGGACTACT | CCAAGGGAAT | 1600 |

FIG. 8b

| | | | | | |
|---|---|---|---|---|---|
| CTGTAAAGAA | ATATATACTT | GAGTGGTGTG | TGTTATCAGA | TAAAGCACCC | 1650 |
| TGTATCACAG | ACTGGCAACA | AGAAGATGGT | ACCGTGCATC | GCACCTATTT | 1700 |
| AAGAGGGAAC | TTAGCAGAGA | GCAAATGCTA | TTTGATAACA | GTTACTCCAG | 1750 |
| TATATGCTGA | TGGACCAGGA | AGCCCTGAAT | CCATAAAGGC | ATACCTTAAA | 1800 |
| CAAGCTCCAC | CTTCCAAAGG | ACCTACTGTT | CGGACAAAAA | AAGTAGGGAA | 1850 |
| AAACGAAGCT | GTCTTAGAGT | GGGACCAACT | TCCTGTTGAT | GTTCAGAATG | 1900 |
| GATTTATCAG | AAATTATACT | ATATTTTATA | GAACCATCAT | TGGAAATGAA | 1950 |
| ACTGCTGTGA | ATGTGGATTC | TTCCCACACA | GAATATACAT | TGTCCTCTTT | 2000 |
| GACTAGTGAC | ACATTGTACA | TGGTACGAAT | GGCAGCATAC | ACAGATGAAG | 2050 |
| GTGGGAAGGA | TGGTCCAGAA | TTCACTTTTA | CTACCCCAAA | GTTTGCTCAA | 2100 |
| GGAGAAATTG | AAGCCATAGT | CGTGCCTGTT | TGCTTAGCAT | TCCTATTGAC | 2150 |
| AACTCTTCTG | GGAGTGCTGT | TCTGCTTTAA | TAAGCGAGAC | CTAATTAAAA | 2200 |
| AACACATCTG | GCCTAATGTT | CCAGATCCTT | CAAAGAGTCA | TATTGCCCAG | 2250 |
| TGGTCACCTC | ACACTCCTCC | AAGGCACAAT | TTTAATTCAA | AAGATCAAAT | 2300 |
| GTATCCAGAT | GGCAATTTCA | CTGATGTAAG | TGTTGTGGAA | ATAGAAGCAA | 2350 |
| ATGACAAAAA | GCCTTTTCCA | GAAGATCTGA | AATCATTGGA | CCTGTTCAAA | 2400 |
| AAGGAAAAAA | TTAATACTGA | AGGACACAGC | AGTGGTATTG | GGGGGTCTTC | 2450 |
| ATGCATGTCA | TCTTCTAGGC | CAAGCATTTC | TAGCAGTGAT | GAAAATGAAT | 2500 |
| CTTCACAAAA | CACTTCGAGC | ACTGTCCAGT | ATTCTACCGT | GGTACACAGT | 2550 |
| GGCTACAGAC | ACCAAGTTCC | GTCAGTCCAA | GTCTTCTCAA | GATCCGAGTC | 2600 |
| TACCCAGCCC | TTGTTAGATT | CAGAGGAGCG | GCCAGAAGAT | CTACAATTAG | 2650 |
| TAGATCATGT | AGATGGCGGT | GATGGTATTT | TGCCCAGGCA | ACAGTACTTC | 2700 |
| AAACAGAACT | GCAGTCAGCA | TGAATCCAGT | CCAGATATTT | CACATTTTGA | 2750 |
| AAGGTCAAAG | CAAGTTTCAT | CAGTCAATGA | GGAAGATTTT | GTTAGACTTA | 2800 |
| AACAGCAGAT | TTCAGATCAT | ATTTCACAAT | CCTGTGGATC | TGGGCAAATG | 2850 |
| AAAATGTTTC | AGGAAGTTTC | TGCAGCAGAT | GCTTTTGGTC | CAGGTACTGA | 2900 |
| GGGACAAGTA | GAAAGATTTG | AAACAGTTGG | CATGGAGGCT | GCGACTGATG | 2950 |
| AAGGCATGCC | TAAAAGTTAC | TTACCACAGA | CTGTACGGCA | AGGCGGCTAC | 3000 |
| ATGCCTCAGT | GAAGGACTAG | TAGTTCCTGC | TACAACTTCA | GCAGTACCTA | 3050 |
| TAAAGTAAAG | CTAAAATGAT | TTTATCTGTG | AATTC | | 3085 |

FIG. 9a

Met Leu Ala Val Gly Cys Ala Leu Leu Ala Ala Leu Leu Ala Ala Pro
            5                   10                  15
Gly Ala Ala Leu Ala Pro Arg Arg Cys Pro Ala Gln Glu Val Ala Arg
            20                  25                  30
Gly Val Leu Thr Ser Leu Pro Gly Asp Ser Val Thr Leu Thr Cys Pro
            35                  40                  45
Gly Val Glu Pro Glu Asp Asn Ala Thr Val His Trp Val Leu Arg Lys
            50                  55                  60
Pro Ala Ala Gly Ser His Pro Ser Arg Trp Ala Gly Met Gly Arg Arg
65                  70                  75                  80
Leu Leu Leu Arg Ser Val Gln Leu His Asp Ser Gly Asn Tyr Ser Cys
                85                  90                  95
Tyr Arg Ala Gly Arg Pro Ala Gly Thr Val His Leu Leu Val Asp Val
            100                 105                 110
Pro Pro Glu Glu Pro Gln Leu Ser Cys Phe Arg Lys Ser Pro Leu Ser
            115                 120                 125
Asn Val Val Cys Glu Trp Gly Pro Arg Ser Thr Pro Ser Leu Thr Thr
            130                 135                 140
Lys Ala Val Leu Leu Val Arg Lys Phe Gln Asn Ser Pro Ala Glu Asp
145                 150                 155                 160
Phe Gln Glu Pro Cys Gln Tyr Ser Gln Glu Ser Gln Lys Phe Ser Cys
            165                 170                 175
Gln Leu Ala Val Pro Glu Gly Asp Ser Ser Phe Tyr Ile Val Ser Met
            180                 185                 190
Cys Val Ala Ser Ser Val Gly Ser Lys Phe Ser Lys Thr Gln Thr Phe
            195                 200                 205
Gln Gly Cys Gly Ile Leu Gln Pro Asp Pro Pro Ala Asn Ile Thr Val
210                 215                 220

FIG. 9b

Thr Ala Val Ala Arg Asn Pro Arg Trp Leu Ser Val Thr Trp Gln Asp
225                     230                     235                     240
Pro His Ser Trp Asn Ser Ser Phe Tyr Arg Leu Arg Phe Glu Leu Arg
            245                     250                     255
Tyr Arg Ala Glu Arg Ser Lys Thr Phe Thr Thr Trp Met Val Lys Asp
            260                     265                     270
Leu Gln His His Cys Val Ile His Asp Ala Trp Ser Gly Leu Arg His
        275                     280                     285
Val Val Gln Leu Arg Ala Gln Glu Glu Phe Gly Gln Gly Glu Trp Ser
    290                     295                     300
Glu Trp Ser Pro Glu Ala Met Gly Thr Pro Trp Thr Glu Ser Arg Ser
305                     310                     315                     320
Pro Pro Ala Glu Asn Glu Val Ser Thr Pro Met Gln Ala Leu Thr Thr
            325                     330                     335
Asn Lys Asp Asp Asp Asn Ile Leu Phe Arg Asp Ser Ala Asn Ala Thr
            340                     345                     350
Ser Leu Pro Val Gln Asp Ser Ser Ser Val Pro Leu Pro Thr Phe Leu
        355                     360                     365
Val Ala Gly Gly Ser Leu Ala Phe Gly Thr Leu Leu Cys Ile Ala Ile
        370                     375                     380
Val Leu Arg Phe Lys Lys Thr Trp Lys Leu Arg Ala Leu Lys Glu Gly
385                     390                     395                     400
Lys Thr Ser Met His Pro Pro Tyr Ser Leu Gly Gln Leu Val Pro Glu
            405                     410                     415
Arg Pro Arg Pro Thr Pro Val Leu Val Pro Leu Ile Ser Pro Pro Val
            420                     425                     430
Ser Pro Ser Ser Leu Gly Ser Asp Asn Thr Ser Ser His Asn Arg Pro
        435                     440                     445
Asp Ala Arg Asp Pro Arg Ser Pro Tyr Asp Ile Ser Asn Thr Asp Tyr
        450                     455                     460
Phe Phe Pro Arg
465

PHARMACEUTICAL COMPOSITION FOR TREATING HEPATITIS B VIRUS (HBV) INFECTION

CROSS-REFERENCE TO RELATED APPLICATIONS

This application is a continuation-in-part of U.S. Ser. No. 08/795,473, filed Feb. 11, 1997, now U.S. Pat. No. 6,217,858 which is incorporated by reference herein in its entirety.

BACKGROUND OF THE INVENTION

The present invention relates to pharmaceutical compositions for the treatment of hepatitis B virus (HBV) infection.

HBV infection in humans can cause chronic liver disease which will, in some cases, proceed to hepatocellular carcinoma. The initial steps of HBV attachment to cells and the targeting of the viral genome to the host cell nucleus have yet to be deciphered. The specific receptor for HBV has not so far been identified, even though various serum proteins and cellular membrane glycoproteins have been suggested as mediators of cell penetration or viral receptors. HBV envelope proteins were reported to contain residues which interact with polymerized albumin [P. Pontisso, et al., *Journal of Virology*, Vol. 63, No. 1981–1, p. 988 (1981)] or with soluble transferring [M. Gagliardi, et al., *Eur. J. Immunol.*, Vol. 24, pp. 1372–1376 (1994)], enabling viral penetration of cells via their respective receptors, probably in a non-specific manner.

In a study reported by Neurath, et al. [A. Neurath, et al., *J. Exp. Med.*, Vol. 175, pp. 461–469 (1992)] hIL-6 was shown to bind the pS1 (aa 21–47) segment of the HBV envelope. Putative candidates for the HBV receptor were recently reported, including Annexin V (endohexin II) [K. Hertogs, et al., *Virology*, Vol. 197, pp. 549–557 (1993)]; apolipoprotein H [H. Mehdi, et al., *Journal of Virology*, Vol. 68, pp. 2415–2424 (1994)]; and asialoglycoprotein receptor [U. Treichel, et al., *Journal of General Virology*, Vol. 75, pp. 3021–3029 (1994)].

Binding experiments have demonstrated that the pre-SI (pS1)region of the viral envelope protein contains a recognition site for the host cell [A.R. Neurath, et al., *Cell*, Vol. 46, pp. 429–436 (1986); M. Petit, et al., *Virology*, Vol. 180, pp. 483–491 (1990); M. Petit, et al., *Virology*, Vol. 197, pp. 211–222 (1992)]. Although previous studies had suggested that HepG2 cells [R. Bchini, et al., *Journal of Virology*, Vol. 64, pp. 3025–3032 (1991)] and human hepatocytes [P. Gripon, et al., *Journal of Virology*, Vol. 62, pp. 4136–4143 (1988); T. Ochiya, et al., *Proc. Natl. Acad. Sci. U.S.A.*, Vol. 86, pp. 1875–1879 (1989); P. Gripon, et al., *Virology*, Vol. 192, pp. 534–540 (1993); P. Galle, et al., *Gastroenterology*, Vol. 106, pp. 664–673 (1994)] could support HBV infection in vitro, no cellular receptor has as yet been defined in either system, and these models were of low experimental reproducibility.

In current reports, it has been shown that a chimeric mouse, generated by using Beige/Nude/X linked immunodeficient (BNX) mice, preconditioned by total body irradiation (12Gy) and reconstituted with severe combined immunodeficient (SCID) mice bone marrow (BM) cells, is permissive for normal human T and B cells [I. Lubin, et al., *Science*, Vol. 252, pp. 427–431 (1991)], as well as for normal human liver tissue [E. Galun, et al., *Journal of Infectious Diseases*, Vol. 175, pp. 25–30 (1995)]. Hepatitis C virus (HCV) viremia was detectable for up to two months, after implantation under the kidney capsule of the BNX>SCID chimeric animals of either a human liver fragment with preexisting HCV infection, or normal human liver tissue following incubation ex-vivo of the transplanted liver fragment with HCV-positive sera [E. Galun, et al., ibid.].

Earlier studies have revealed that human interleukin 6 (hIL6) contains recognition sites for the hepatitis B virus (HBV). Chinese hamster ovary cells transfected with human IL-6 cDNA and Spondoptera frugiperdaovarian insect cells infected with recombinant baculovirus carrying human IL-6 cDNA expressed receptors for the preS921-47) region of the HBV envelope protein, indicating that expression of IL-6 sequences encompasses a binding site for the HBV envelope protein. Thus, the possibility of developing antiviral compounds mimicking the receptor binding site for HBV on IL-6 but not displaying undesirable biological effects of the intact IL-6 molecule was raised, because it was found that the interaction between the preS1 region of the HBV envelope proteins and cells of hepatic origin was inhibited by IL-6 and by anti-IL-6 antibodies [A. Neurath, et al., *J. Exp. Med.* Vol. 176, pp. 1561–1569 (1992)].

Heretofore, one of the major obstacles in elucidating the initial steps of HBV infection and the assessment of antiviral agents, has been the lack of a small animal model. Using the techniques referred to above, it was possible to develop SCID>BNX animals which sustain HBV viremia following the implantation of an ex-vivo HBV DNA-positive sera incubation with liver tissue. The method in which the animals were prepared for the experiments described herein, and the surgical technique for transplantation, are similar to those previously reported [E. Galun, et al., ibid.].

As described, e.g., in PCT/US94/05410, it has now been found, using a chimeric animal model, that human interleukin 6 (hIL6) is essential for HBV infection. Having identified that hIL6 serves as an essential bridge for HBV infection, the invention now provides a pharmaceutical composition for the treatment of hepatitis B virus infection, comprising an amount of a soluble active agent which interacts with at least one of the binding sites between hIL6 and pS1 and between hIL6 and hepatocytes and other HBV-permissive cells, said active agent being present in sufficient amount to competitively bind to at least one of said sites and thereby to prevent hIL6-mediated HBV infection of hepatocytes and other HBV-permissive cells.

In a first preferred embodiment of the present invention, there is provided a pharmaceutical composition for the treatment of hepatitis B virus (HBV) infection, comprising an amount of soluble gp80 and/or gp130 receptor sites sufficient to inhibit the binding of hIL6 to hepatocytes and other HBV-permissive cells.

In a second preferred embodiment of the present invention, there is provided a pharmaceutical composition for the treatment of HBV infection, comprising an amount of soluble amino acid sequences corresponding to amino acids 21 to 46 of pS1 to block the interaction of HBV with hIL6.

In a third preferred embodiment of the present invention, there is provided a pharmaceutical composition for the treatment of HBV infection, comprising an amount of a soluble ligand selected from the group consisting of peptides LYS41-ALA56, GLY77-GLU95 and GLN153-HIS165 to block the interaction of hIL6 with hepatocytes and other HBV-permissive cells.

In a fourth preferred embodiment of the present invention, there is provided a pharmaceutical composition for the treatment of HBV infection, comprising hIL6 conjugated with an anti-viral agent. In a preferred embodiment, the anti-viral agent conjugated to hIL6 comprises glycoprotein 80 or a portion thereof. In a preferred embodiment of the invention, the hIL6-anti-viral agent conjugate is Hyper-IL6 (HIL6).

In yet another preferred embodiment of the invention, there is provided a pharmaceutical composition for the treatment of hepatitis B virus (HBV) infection of hepatocytes, comprising a soluble active agent which competitively interacts with at least one of the binding sites between human interleukin 6 (hIL6) and hepatocytes, said soluble active agent being selected from the group consisting of glycoprotein 80 (gp80) having receptor sites which interact with hIL6, soluble glycoprotein 130 (gp130) having receptor sites which interact with hIL6, hIL6 derived peptide LYS41-ALA56, hIL6 derived peptide GLY77-GLU95, hIL6 derived peptide GLN153-HIS165, a combined β1 and β2 hIL6 mutant (mhIL6β1+β2), and mhIL6β1+β2 substituted with phe 171 to leu and ser 177 to arg, and mixtures of any of the foregoing. In certain preferred embodiments, such a pharmaceutical composition includes an effective amount of the soluble active agent to treat infection of the hepatocytes by HBV.

In yet another preferred embodiment of the invention, there is provided a pharmaceutical composition for the treatment of hepatitis B virus (HBV) infection of hepatocytes, comprising a soluble active agent which disrupts the hIL6/hIl6Rα complex with hIL6Rβ.

In yet another preferred embodiment of the invention, there is provided a pharmaceutical composition for the treatment of hepatitis B virus (HBV) infection of hepatocytes, comprising a soluble active agent selected from the group consisting of glycoprotein 80 (gp80) having receptor sites which interact with hIL6, soluble glycoprotein 130 (gp130) having receptor sites which interact with hIL6, hIL6 derived peptide LYS41-ALA56, hIL6 derived peptide GLY77-GLU95, hIL6 derived peptide GLN153-HIS165, a combined β1 and β2 hIL6 mutant (mhIL6β1+β2), mhIL6β1+β2 substituted with phe 171 to leu and ser 177 to arg, a soluble active agent which disrupts the hIL6/hIl6Rα complex with hIL6Rβ, and mixtures of any of the foregoing.

In general with respect to the pharmaceutical compositions described above, the soluble active agent is included in an amount effective to treat HBV infection of hepatocytes, e.g., the soluble active agent is present in an amount from about 100 ng/kg to about 100 mg/kg, based on the body weight of the patient. In preferred embodiments, such a pharmaceutical composition includes a soluble active agent in an amount from about 10 μg/kg to about 10 mg/kg, based on the body weight of the patient.

The invention is further directed to a method for treatment of infection of hepatocytes with HBV, comprising administering to a human patient a soluble active agent which inhibits the interaction between human interleukin 6 (hIL6) and hepatocytes. In certain preferred embodiments of the method, the active agent competitively interacts with at least one of the binding sites. In such preferred embodiments, it is further preferred that the soluble active agent comprises a soluble glycoprotein 80 (gp80) and/or soluble glycoprotein 130 (gp 130) having receptor sites which bind to hIL6 and competitively inhibit the interaction between hIL6 and hepatocytes. In other preferred embodiments of the method, it is further preferred that the soluble active agent comprises a soluble ligand selected from the group consisting of peptides LYS41-ALA56, GLY77-GLU95 and GLN153-HIS165 and competitively blocks the interaction of hIL6 with hepatocytes. In yet other preferred embodiments of the method, it is further preferred that the soluble active agent disrupts the hIL6/hIl6Rα complex with hIL6Rβ. In other preferred embodiments of the method, it is further preferred that the soluble active agent is selected from the group consisting of hIL6 derived peptide LYS41-ALA56, hIL6 derived peptide GLY77-GLU95, hIL6 k) derived peptide GLN153-HIS165, a combined β1 and β2 hIL6 mutant (mhIL6β1+β2), and mhIL6β1+β2 substituted with phe 171 to leu and ser 177 to arg, and mixtures of any of the foregoing. In any of the preferred methods, it is preferred that the soluble active agent is administered in an amount from about 100 ng/kg to about 100 mg/kg per day, and in certain embodiments from about 10 μg/kg to about 10 mg/kg, based on the body weight of the patient.

The invention is further directed to the use of a soluble active agent which inhibits the interaction between human interleukin 6 (hIL6) and hepatocytes for the treatment of infection of hepatocytes with HBV. In certain preferred embodiments, the active agent competitively interacts with at least one of the binding sites. In such preferred embodiments, it is further preferred that the soluble active agent comprises a soluble glycoprotein 80 (gp80) and/or soluble glycoprotein 130 (gp130) having receptor sites which bind to hIL6 and competitively inhibit the interaction between hIL6 and hepatocytes. Alternatively or in addition thereto, the soluble active agent comprises a soluble ligand selected from the group consisting of peptides LYS41-ALA56, GLY77-GLU95 and GLN153-HIS165 and competitively blocks the interaction of hIL6 with hepatocytes. In yet other preferred embodiments, it is further preferred that the soluble active agent disrupts the hIL6/hIl6Rα complex with hIL6β. Alternatively or in addition thereto, in other preferred embodiments, it is further preferred that the soluble active agent is selected from the group consisting of hIL6 derived peptide LYS41-ALA56, hIL6 derived peptide GLY77-GLU95, hIL6 derived peptide GLN153-HIS165, a combined β1 and β2 hIL6 mutant (mhIL6β1+β2), and mhIL6β1+β2 substituted with phe 171 to leu and ser 177 to arg, and mixtures of any of the foregoing. Alternatively or in addition to the competitively active soluble active agents identified in this above paragraph, the soluble active agent may comprise anti-viral agents conjugated with hIL-6, which inhibit HBV (e.g. 3TC, Famciclovir and FIAU analogues); a toxin which exerts cellular toxicity only to cells expressing IL-6R (e.g., the chimeric fusion toxin $DAB_{389}$-IL-6); monoclonal antibodies specific for hIL-6 which bind either at site I or site II on the IL-6 protein; a minibody polypeptide (e.g., MB02) which binds tightly and specifically to hIL-6 and is an effective inhibitor of the cytokine's biological activity; an anti-IL-6R mAb, and mixtures of any of the foregoing. In any of the embodiments described in this paragraph, it is preferred that the soluble active agent is administered an effective amount to treat HBV infection of the hepatocytes. This effective amount will generally be, e.g., an amount from about 100 ng/kg to about 100 mg/kg per day, and in certain embodiments from about 10 μg/kg to about 10 mg/kg, based on the body weight of the patient. Further, the examples provided in this paragraph are not meant to be exclusive. Many other soluble active agents will be readily apparent to one skilled in the art having the benefit of reading this specification.

For purposes of the present invention, the term hIL-6 is human interleukin 6; the term pS1 stands for pre-S1; gp80 is glycoprotein 80 (also referred to as hIL-6R or hIL-6Rα); and gp130 is glycoprotein 130, otherwise known as hIL-6Rβ (human interleukin 6 receptor beta).

For purposes of the present invention, the terms "bind" and "interact" shall be interchangeable.

BRIEF DESCRIPTION OF THE DRAWINGS

The patent or application file contains at least one drawing executed in color. Copies of this patent or patent application publication with colro drawing(s) will be provided by the Office upon request and payment of the necessary fee.

FIG. 5 provides the nucleotide sequence for hIL-6 mRNA;

FIGS. 6a–d provide the nucleotide sequence for hIL-6 receptor mRNA;

FIG. 7 provides the nucleotide sequence for the IL-6 receptor;

FIGS. 8 and 8a provide the nucleotide sequence for gpl130;

FIGS. 9a–b provide the nucleotide sequence for hIL-6 receptor alpha;

Figure 1:
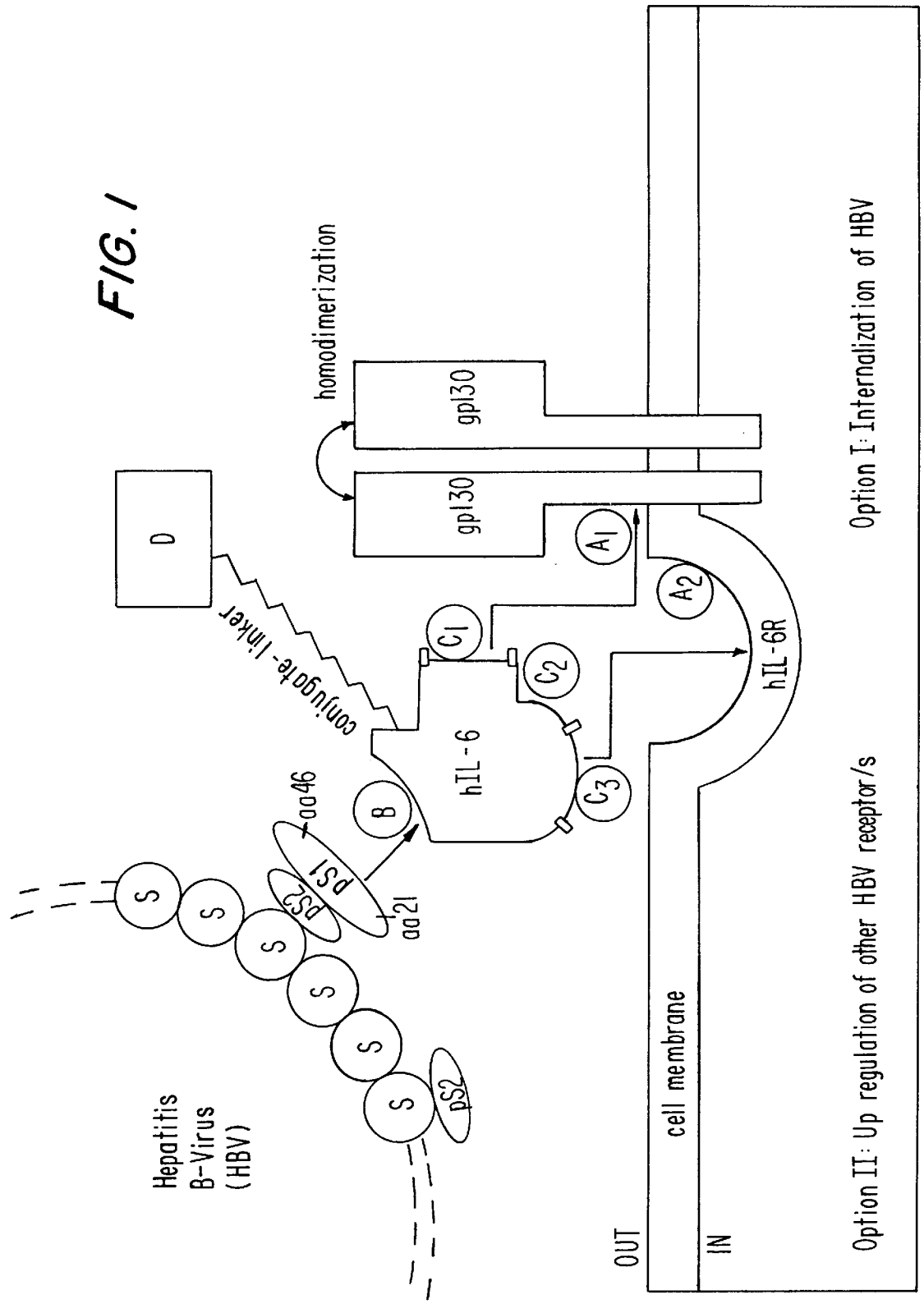
FIG. 1 depicts the mechanism of the hIL6 signal transduction cascade, as contemplated herein.

Research on the mechanism of HBV entry into host cells reveals a vast number of viral binding sites, intermediary molecules interacting with the virus or the target cell membrane and host cell surface molecules. All have been suggested to have a role in HBV infection. A summary of the published data on the factors participating in the HBV binding to cells is shown in Table 1.

TABLE 1

| Reference | Viral binding site | Intermediary molecule | Cell surface binding site |
|---|---|---|---|
| Pontisso, Gastroenter 84:220, 1983 | HBsAg (P31) | Polymerized human albumin | albumin binding glycoprotein |
| Machida, Gastroenter 85:268, 1983 | | | |
| Pontisso, J Virol Meth 6:151, 1983 | | | |
| Michel, PNAS (USA) 81:7708, 1984 | | | |
| Machida, Gastroenter 86:910, 1984 | pre-S (P8) pre-S2 | Polymerized human albumin | |
| Pontisso, J Virol 63:1981, 1989 | | | |
| Neurath, Cell 46:429, 1986 | pre-S1 | (direct binding) | (binding to HepG2 Cells) |
| Petit, Mol Immunol 26:531, 1989 | | | |
| Neurath, Vaccine 7:234, 1989 | | | |
| Neurath, Virology 176:448, 1990 | | | |
| D'Mello, Virology 237:319, 1997 | | | |

TABLE 1-continued

| Reference | Viral binding site | Intermediary molecule | Cell surface binding site |
|---|---|---|---|
| Peeples, Virology 160:135, 1987 Komai, Virology 177:332, 1990 | HBsAg | (direct binding) | (binding to Vero cells) |
| Pontisso, J Gen Virol 73:2041, 1992 | pre-S1 | (direct binding) | IgA receptor |
| Komai, Virology 163:629, 1988 | HB5Ag | (direct binding) | asialoglycoprotein |
| Dash, Hepatology 13:134, 1991 | pre-S2 | (direct binding) | |
| Neurath, J Exp Med 175:461, 1992 | pre-S1 | IL-6 | |
| Petit, Virology 187:211, 1992 | pre-S1 | pre-S1 binding protein | |
| Franco, J Exp Med 175:1195, 1992 | pre-S2 | | Transferrin receptor |
| Dash, J Med Virol 37:116, 1992 | pre-S1 | (direct binding) | 31kD |
| Budkowska, J Virol 67:4316, 1993 | pre-S1 & pre-S2 | HBV binding factor | — |
| Gagliardi, Eur J Immun. 24:1372, 1994 | — | Soluble Transferrin | Transferrin receptor |
| Treichel, J Gen Virol 75:3021, 1994 | pre-S1 | (direct binding) | asialoglycoprotein receptor |
| Hertogs, Virology 197:549, 1993 | HBsAg | (direct binding) | Endonexin II |
| Mehdi, J Virol 68:2415, 1994 | HBsAg | Apolipoprotein-H | Apolipoprotein-H receptor |

The information presented in Table 1 summarizes most, if not all, of the known viral and cell membrane factors participating in HBV host cell binding. However, the information provided in the underlying studies from the references identified in Table 1 and other studies reported by the investigators cited have benn able to reproducibly show any experiments of HBV fusion, initial steps of viral entry or infection through any of the suggested specific viral, intermediary or cellular factors so far in tissue culture.

Although the viral structures involved in attachment to the target cell have been identified, the cellular receptor(s) for HBV has not yet been determined and the biochemical events leading to infection remained unknown until the present invention. It is believed that one of the main reasons for the lack of knowledge on the early states of HBV binding and internalization is that most research groups were not able to infect human hepatocytes or human hepatoma cell lines. Thus, although numerous publications have taught various cell surface binding sites, with and without intermediaries, none of said publications teach an interaction leading to infection. The present invention, for the first time, teaches that hIL-6 is the essential intermediary for HBV infection through the hIL-6 binding to hepatocytes and that blockage of the interaction between any of said components is sufficient to block infection.

In accordance with the present invention, it must be recognized that viral binding to target cells is a multiple step process where not all partners are always essential for fusion and infection. Viral tropism depends on a range of factors which influence the interaction between a virus and cells. As has been shown for HIV and other viruses, the presence of a putative viral receptor may be insufficient to allow viral entry into the host cell. In addition, for a number of viruses more than one receptor expressed on the cell surface has been found to be essential for a productive infection of a targeted cell. The viral binding to target cells and penetration of cell membranes is probably a multiple step cascade event. The virus interacts with more than one receptor molecule for the first step of cell membrane attachment. Following viral attachment for the group of envelope viruses, such as HBV, penetration of cytoplasmic membrane takes place after fusion between the viral envelope and cell membrane.

FIG. 1 depicts the mechanism of the hIL6 signal transduction cascade, as contemplated herein. The HBV envelope consists of three distinct coterminal proteins which are encoded by a single env gene. The domains of these proteins encoded by the pre-S region of the viral genome represent potential attachment sites of HBV to hIL6 (and have previously been reported to bind directly to hepatocytes, but without causing infection). The crucial HBV binding site has been reported to be located within the amino acid sequence 21 to 47 of the pre-S1 domain and the auxiliary binding site is within the pre-S2 amino acid sequence 120 to 145. hIL-6 exhibits its action on target cells (including hepatocytes) by acting through a receptor complex consisting of a specific hIL-6-binding protein (hIL-6R) and a signal-transducing subunit (gp 130). Soluble forms of the IL-6R (sIL-6R) and gp 130 (sgp 130) are found in different body fluids. The hIL-6/hIL-6R complex induces the homodimerization of two gp 130 molecules leading to a number of intracellular signaling events, reportedly including activation of the transcription factor NF-IL-6, probably via the ras-microtubulus-associated protein (MAP) kinase cascade and activation of the Jak/STAT signaling pathway. Binding of the hIL-6/hIL-6Rα complex to gp 130 gives rise to a hexameric receptor complex made of two hIL-6, two hIL-6Rα, and two gp 130 subunits. It is believed that this complex (including the HBV bound to the hIL6) is internalized into the hepatocyte, thereby causing infection.

Interference of linkages (interactions) at any one of the sites designated as A1, A2, C1, C2, C3 and B will treat and/or prevent HBV infection, in accordance with the present invention. Therefore, conjugating anti-viral agents to any one of the components of the IL-6 complex, which internalizes following the cascade interaction depicted in FIG. 1, can be used to suppress infection. Thus, e.g., the following agents identified in Table 2 can be introduced as anti-HBV agents. Table 2 below, to be read in conjunction with FIG. 1, correlates the interfering agent and site of interaction/compound.

TABLE 2

| Interfering Agent | Site of Interaction/Compound |
| --- | --- |
| A1 | Truncated sIL-6Ra |
| A2 | Truncated sIL-6Ra |
| C1 | Lys41-Ala56 Site 2a (b2) |
| C2 | Gly77-Glu95 Site 2c |
| C3 | Gln153-His165 Site 3 (b1) |
| B | Pre S1 |
| D | IL-6 antiviral conjugate/fusion |

Based on the present discovery that hIL6 acts to mediate HBV infection, it is possible to prepare an antiviral/anti-HBV agent. A pharmaceutical composition for the treatment and/or prevention of HBV infection, comprising an active ingredient having an amino acid sequence similar to hIL6, is thus developed. The hIL6 domain which interacts with hIL6Rα® (® for receptor) and/or hIL6Rβ (amino acid residues: 40–60, 70–100 and 135–175) antagonizes hIL6 interaction to prevent HBV infection.

In view of the fact that the present invention recognizes for the first time the role of hIL6 in HBV infection, it is self-evident to persons skilled in the art that administration of a soluble active agent which interacts with at least one of the binding sites between hIL6 and pS1 and between hIL6 and between hIL6 and hepatocytes and other HBV-permissive cells, such as the active agents enumerated herein, can prevent hIL6-mediated HBV infection. For example, it is well known in the literature that nucleoside analogues are anti-viral agents which inhibit HBV (e.g. 3TC, Famciclovir and FIAU analogues). Furthermore, the conjugation of agents to IL6 was also well known in the art at the time of the filing of the present application.

For example, the chimeric fusion toxin $DAB_{389}$-IL-6, engineered by fusion of a truncated diphtheria toxin structural gene in which the region encoding the native receptor-binding domain was removed and replaced with the gene encoding IL-6, exerts cellular toxicity only to cells expressing IL-6R [R. Masood, et al., Aids Research and Human Retroviruses, Vol. 10, No. 8 (1994)]. Accordingly, $DAB_{389}$-IL-6 and similarly functioning agents are useful in the present invention.

Further, it is known that neutralizing monoclonal antibodies specific for hIL-6 bind two distinct sites on the IL-6 protein (sites I and II). Site I is reported to be a receptor binding site of IL-6, whereas site II is reported to be important for signal transduction. Mutagenesis of site II could therefore result in the isolation of IL-6 receptor antagonists. The mutant protein is inactive because the complex of the gp80 receptor and the mutant protein cannot associate with the signal transducer gp 130. [J. Brakenhoff, et al., J. Biological Chemistry, Vol. 269, pp. 86–93 (1994)]. Thus, hIL-6 antagonist proteins would be useful in the present invention.

Other researchers have identified hIL-6 variants that behave as potent cytokine receptor super-antagonists carrying substitutions that abolish interaction with gp 130 at either site II alone, or at both sites II and III (which is also reported to be involved in signal transduction [E. Sporeno, et al, Blood, Vol. 87, No. 11: pp. 4510–4519 (1996)]. Such agents are useful in the present invention.

Other researchers have identified a minibody polypeptide (MB02) which binds tightly and specifically to hIL-6 and is an effective inhibitor of the cytokine's biolgyical activity [F. Martin, et al., EMBO Journal Vol. 13, No. 22: pp 5303–5309 (1994)]. Such agents are useful in the present invention.

Still further, anti-IL-6 mAb or anti-IL-6R mAb would be useful in the compositions and methods of the invention. Anti-hIL-6 mAb (MH166) has been shown to be capable of neutralizing IL-6 activity. Anti-hIL-6R mAb has been shown to inhibit the binding of IL-6 to the receptor. [Y. Mizutani, et al. Cancer Research 55, 590–596 (1995)]. Monoclonal antibodies to hIL-6 or to hIL-6R are useful in the compositions and methods of the invention.

The molecular analysis of hIL6 binding sites with gp130 and gp80 revealed a number of structural targets on hIL6 which can serve as hIL6 antagonists. The preferable target for an hIL6 antagonist is to disrupt the hIL6/hIL6Rα complex with hIL6Rβ.

Based on previous publication, a number of domains essential for hIL6 activity were reported:
1. Lys41-ala56 (site 2a, also named β2) is involved in the activation of signal-transduction.
2. Gly77-glu95 (site 2c) is important for interaction with hIL6Rα, subunit gp80.
3. Gln153-his165 (site β1), substitution of trp158 to arg or glnl160 to glu combined with thr163 to pro-antagonize the biological activity of hIL6.

4. A combined β1 and β2 hIL6 mutant (mhIL6β1+β2) is inactive on XG-1 hIL6 responsive cells, with a weakly antagonizing activity.

5. The addition of two substitutions to the mhIL6 (m for mutant) β1+β2, phe171 to leu and ser177 to arg, resulted in an increase in the affinity to hIL6Rα, while inhibiting its activity on XG-1 cells.

Based on techniques known per se to persons skilled in the art, the proteins and peptides for use in the pharmaceutical compositions of the present invention are readily prepared, e.g., by the following techniques and steps:

Amplification of chosen segment of DNA from plasmid containing HBV DNA (adw2)-adw HTD by PCR, using primers constructed so as to introduce BamH1 and EcoR1 sites compatible to the pGEX-2T (Pharmacia, Uppsala, Sweden, Catalogue No. 27-4801-01) insertion site. This GST fusion vector provides a system in which fusion proteins are easily purified from the bacterial lysates and can be detected directly as a fusion protein or after cleavage with site specific proteases. After introduction of DNA into pGEX-2T, competent *E. coli* (JM109) are transformed and cloned (LB+10 μg/ml ampicillin). Protein expression is induced by the addition of IPTG (0.1 mM, isopropyl-1-thio-b-D- galactoside) for 1–2 hours. Fusion protein is removed from lysed (sonicated) cells by collection on glutathione-agarose beads (Pharmacia) and eluted from beads using reduced glutathione (5 mM in 50 mM Tris-Cl, pH 8.0). Identification and determination of protein can be done either by use of antibodies to GST or by specific recognition of inserted protein. The complete HBV pS1 protein (aa 1 to aa 119, applying PCR with the sense and anti-sense primers 5'-CGGGATCCATGGGAGGTTGGTCATC-3'[NT 8+2856–2873, EcoR1 as starting site for nt numbering] and 5'-GGAATTCCACTGCATGGC-3'[nt 6–3210] respectively) and the pS1 attachment site aa21 to aa46 constructs were designed and produced in the pGEX-2T system (compound B in FIG. 1).

Truncated soluble forms of gp80 and gp130 are synthesized using the pGEX-2T system as described for the preparation of pS1 (compound A2 and A1, respectively). hIL6 derived peptides (Lys41-ala56, Gly77-glu95 and Gln153- his165, designated C1, C3 and C2, respectively, in FIG. 1) are synthesized by applying a variety of methods including Merrifield solid-phase synthesis and derived methods or other acceptable genetic engineered methods. The compounds produced are linear or cyclic peptides, or parts of large proteins.

Set forth at FIG. 5 is the nucleotide sequence for human interleukin 6 mRNA (SEQ ID NO 1), as published by L. T. May, et al., "Anti-beta Interferron Antibodies Inhibit the Increased Expression of HLA-B7 mRNA in Tumor Necrosis Factor-Treated Human Fibroblasts: Structural Studies of the beta-2 Interferon Involved," Proc. Nat'l Acad. Sci. U.S.A. 83 (23), 8957–8960 (1986).

FIGS. 6a–d depict the nucleotide sequence for the human interleukin 6 receptor mRNA (SEQ ID NO 2), as published by K. Yamasuki, et al., "Cloning and Expression of the Human Interleukin 6 (BSF-2/ISN beta 2) Receptor," Science 241 (4867), 825–828 (1988).

FIG. 7 depicts the nucleotide sequence the interleukin-6 receptor (SEQ ID NO 3), as published by H. Schooltink, et al., "Structural and Functional Studies on the Human Nepatic Interleukin-6 Receptor," Biochem. J. 277:659–664 (1991).

FIGS. 8a and 8b depict the nucleotide sequence for the gp 130 interleukin 6 receptor (SEQ ID NO 4), as published by Hibi, et al, "Molecular Cloning and Expression of an IL-6 Signal Transducer, gp 130," Cell 63 (6), 1149–1157 (1990).

FIGS. 9a and 9b depict the amino acid sequence for the human interleukin 6 receptor alpha (IL-6R alpha) (SEQ ID NO 5), as published by K. Yamasaki, et al., "Cloning and Expression of the Human Interleukin 6 (BSF-2/ISN beta 2) Receptor," Science 241 (4867), 825–828 (1988).

Compositions according to the present invention can be administered orally or parenterally, including intravenous, intraperitoneal, intranasal and subcutaneous administration. Implants of the compounds are also useful.

The proteins of the present invention are administered in combination with other drugs, or singly, consistent with good medical practice. The composition is administered and dosed in accordance with good medical practice, taking into account the clinical condition of the individual patient, the site and method of administration, scheduling of administration, and other factors known to medical practitioners. The 'effective amount' for purposes herein is thus determined by such considerations as are known in the art.

When administering the compositions parenterally, the pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion, and by the use of surfactants. Non-aqueous vehicles such as cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, anti- oxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent or additive used would have to be compatible with the compounds.

Sterile injectable solutions can be prepared by incorporating the proteins utilized in practicing the present invention in the required amount of the appropriate solvent with various of the other ingredients, as desired.

A pharmacological formulation described and claimed herein can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems, such as polymer matrices, liposomes, and microspheres. An implant suitable for use in the present invention can take the form of a pellet which slowly dissolves after being implanted, or a biocompatible delivery module well-known to those skilled in the art. Such well-known dosage forms and modules are designed such that the active ingredients are slowly released over a period of several days to several weeks.

Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow, implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well-known to those skilled in the art.

A pharmacological formulation of the present invention can be administered orally to the patient. Conventional methods such as administering the compounds in tablets, suspensions, solutions, emulsions, capsules, powders, syrups and the like, are usable. Known techniques which deliver the new compositions orally or intravenously and retain the biological activity, are preferred.

In one embodiment, the new compositions can be administered initially by intravenous injection. The amount of the soluble active agent to be administered is an amount necessary to treat HBV infection in hepatocytes. This effective amount will vary for the patient being treated, and the particular agent used, and will vary from about 100 ng/kg of body weight to 100 mg/kg of body weight per day, and preferably will be from 10 µg/kg to 10 mg/kg per day.

Based on the teachings of the present invention, the concentration of the various components necessary to competitively interact or bind to at least one of the recited sites is readily determined by a person skilled in the art and especially in light of relevant information available before the date of the present invention, as seen, e.g., from the following publications: Cancer Research 55: pp590–596 (1995); EMBO Journal Vol. 13, No. 22: pp. 5303–5309 (1994); J. Exp. Med. Volume 183: pp. 1399–1406 (1996); and Blood, Vol 87, No. 11: pp. 4510–4519 (1996).

EXAMPLES

Human liver tissue was taken from patients undergoing liver surgery for liver diseases, who had HBV viremia of $10^7$–$10^9$ parciles/ml with positive HBV DNA in the liver tissue. The liver tissue was implanted under the kidney capsule of the chimeric animals. Although HBsAg was easily detected in pre-infected HBV DNA positive/HBeAg positive transplanted tissue (FIG. 2), 1–3 months after liver fragment implantation HBV sequences were undetectable by PCR (applying primers spanning the viral core gene as well as the envelope region, at the a determinant of the HBsAg) in any of these experiments. Furthermore, intravenous or intraperitoneal (i.p.) injection of 200 µl of high-titer HBV particles (>$10^8$/ml) following the transplantation of a normal human liver fragment, failed to generate HBV DNA sequences during the next 30 days (data not shown).

Lymphocytes, positive for HBV DNA by dot blot hybridization, were separated by lymphopheresis (Baxter Fenwell CS-3000 Pulse Blood Cell Separators, Deerfield, Ill., U.S.A.) from a patient with HBV-related chronic liver disease whose sera were positive for HBV DNA and HBeAg. Forty million HBV DNA-positive lymphocytes were injected i.p. to each mouse, subsequent to transplantation of normal human liver at the subcapsular site of the kidney. HBV sequences were not detected in the sera of these animals during the following 21 days.

Although the primary infection site for HBV is hepatocytes, lymphocytes and endothelial cells have both been shown to harbor HBV transcripts and viral-related proteins [J. Romet-Lemonne, et al., Science, Vol.221, pp. 667–669 (1983); H. Blum, et al., Proc. Natl. Acad. Sci. U.S.A., Vol. 80, pp. 6685–6688 (1983); E. Galun, et al., American Journal of Pathology, Vol. 145, pp. 1001–1007 (1994)], suggesting a common specific cell membrane receptor mechanism supporting viral penetration. This mechanism would prevent infection of receptor negative cells, despite their being permissive for HBV replication by transfection [E. Galun, et al., Journal of General Virology, Vol. 73, pp. 173–178 (1992)]. All three primary cell types hosting HBV naturally, i.e., hepatocytes, lymphocytes and endothelial cells, respond to hIL6 through the human IL6 receptor (hIL6R) which is expressed on their cell membranes [A. Mackiewicz, et al., The Journal of Immunology, Vol. 149, pp. 2021–2027 (1992); J. Bauer, et al., FEBS Letter, Vol. 249, pp. 27–30 (1989); T. Kishimoto, et al., Science, Vol.258, p.593 (1992)]. Furthermore, as previously shown, hIL6 binds to HBV through pS1.

Figure 3A:
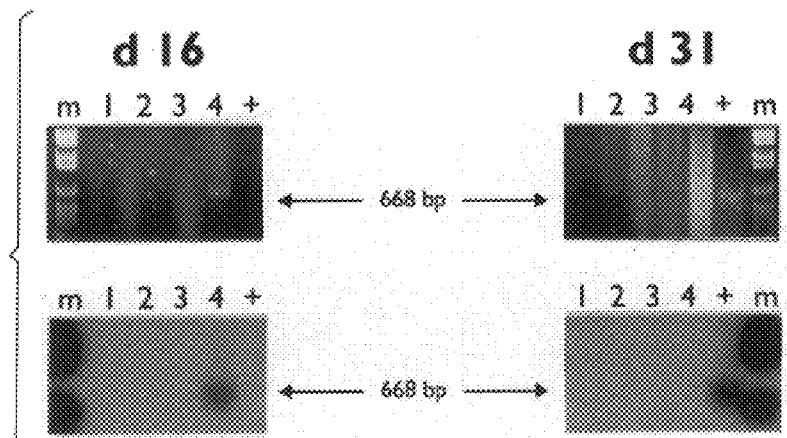
FIGS. 3a–d show that hIL6 mediates HBV viremia in SCID>BNX chimeric mice transplanted with human tissue.

A fragment of normal human liver from a patient with no indication of any HBV-related markers or disease, was incubated ex-vivo with a high titer HBV DNA-positive serum prior to transplantation under the kidney capsule of the chimeric animals. HBV DNA sequences were undetectable by PCR from two different genomic regions in any of these animals during the month following transplantation. Results are shown in FIG. 3A. These results were reproduced in additional experiments in over 50 mice, using four different HBV DNA-positive sera.

Figure 3B:
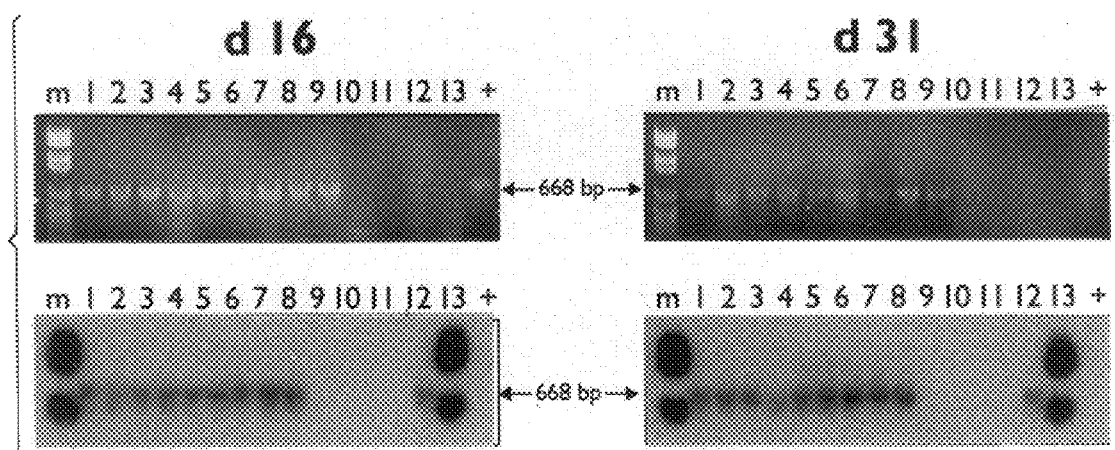

However, when liver tissue originating from the same patients was incubated ex-vivo with the above-mentioned HBV DNA-positive sera together with hIL6, HBV DNA sequences were detected from day 16 to day 31, in sera of about 50% of the transplanted animals. These results are shown in FIG. 3B.

Similar results were obtained in experiments conducted under the above-stated conditions, using additional HBV DNA sera and liver tissue from different sources. In these experiments, HBV DNA sequences could be detected up to day 60 following transplantation (results not shown).

Pre-exposure of liver tissue to hIL6 prior to incubation with HBV ex-vivo, increased infection to about 90% of the animals. Animals positive for HBV sequences in serum at day 31 were also positive for HBsAg in the implanted hepatocytes, as shown in FIG. 3D. Liver fragments incubated ex-vivo with HBV under the above conditions and fixed for immunohistochemical analysis prior to transplantation were negative for HBsAg (results not shown).

Figure 4:
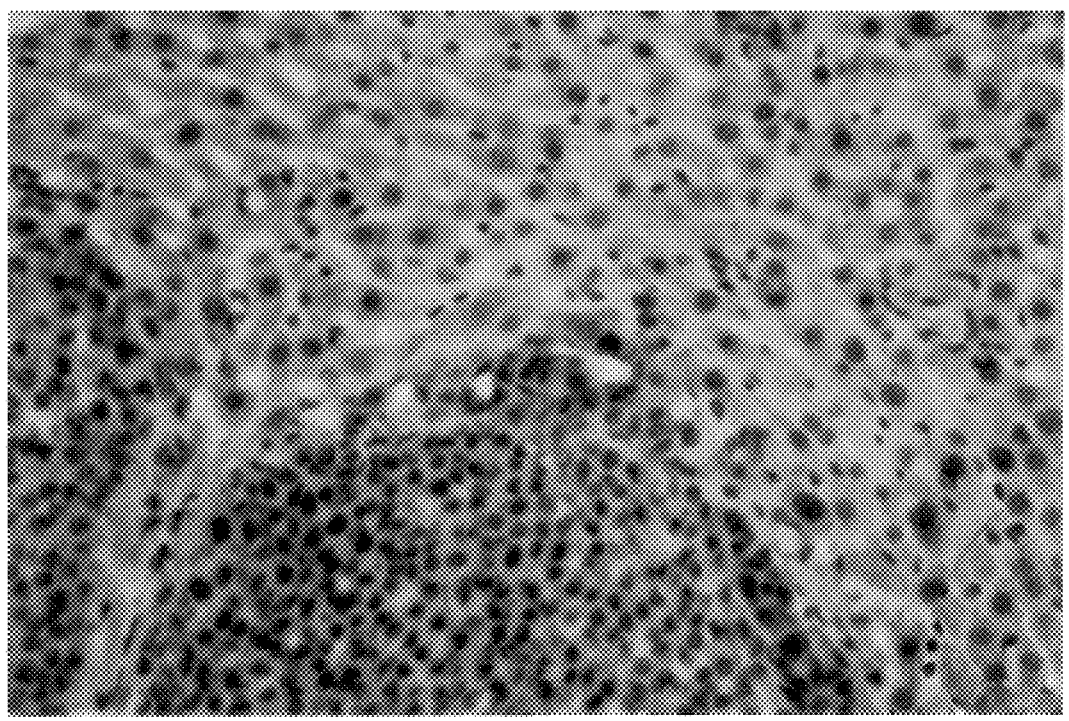
FIG. 4 illustrates the liver histology of a HepG2-hIL-6R tumor, which developed one month following intrasplenic injection into a SCID>BNX chimeric mouse (H and E staining)

To further assess the role of hIL6 in supporting HBV infection, a human hepatoblastoma cell line HepG2 (ATCC HB 8065), an HepG2-derived, stably transfected hIL6R cell line, a null hIL6R (a cell line which does not express hIL6R) named HepG2-PDI and an hIL6 producing line named HepG2-hIL6 [S. Rose-John, et al., The Journal of Biological Chemistry, Vol. 268, pp. 22084–22091 (1993)] were incubated with HBV DNA-positive sera, with or without hIL6. Following incubation, the various mixtures were injected intrasplenically to the chimeric mice to generate HCC foci in the liver, as shown in FIG. 4. The results of these experiments are summarized below in Table 3.

TABLE 3

HBV-DNA as detected by PCR in sera of chimeric mice following intrasplenic injection of HBV, with or without hIL6, after incubation with HepG2-derived cell lines.

| Cell Line | HepG$_2$ hIL6R | | HepG$_2$ PDI | | HepG$_2$ | | HepG$_2$ hIL6 | |
|---|---|---|---|---|---|---|---|---|
| hIL6 | + | − | + | − | + | − | + | − |
| HBV-DNA PCR product | + | − | + | − | + | +/− | + | + |

In this experiment, four separate cell lines were prepared. The four separate cell lines are listed from left to right in Table 3. The first cell line, contained a human hepatoblastoma cell line (HepG2) which expresses the human interleukin 6 receptor ("hIL6R"). The second cell line, HepG2-PDI, which does not express hIL6R. The third cell line, Hep G2, did not produce hIL6. The fourth cell line, known as HepG2-hIL6, produces hIL6. The cell lines were incubated with two sets of HBV-positive DNA sera, one set having hIL6, denoted with a "+" in Table 1, and the other set not having hIL6 and denoted with a "−". The cell lines were injected intrasplenically to chimeric mice. The results showed that HBV-DNA was detected in mice with each of the four cell lines with the DNA having hIL6. In those cell lines incubated with DNA hIL6, HBV-DNA was present only in the mice injected with the cell lines HepG2 and HepG2hIL6. The HepG2 hIL6 cell line expresses hIL6.

The results set forth in Table 3 establish the connection between HBV infection and the preS1 peptide region of the HBV viral envelope, the gp80 and gp130 receptor sites, and human interleukin 6 ("hIL6"), and establish that HBV is mediated by hIL6.

Method:
All cell lines grew in T25 flasks supplemented with DMEM medium, enriched with 10% fetal bovine serum. For infection experiments, cells were trypsinized and washed twice with PBS, followed by incubation with HBV-positive human sera (108 virions/ml) in the presence or absence of hIL6 (500 ng/ml) in 1–2 ml of DMEM. After 2–4 h incubation at 37° C., $4 \times 10^6$ cells/ml, 0.5 ml/mouse were injected intrasplenically to 8–10 SCID>BNX mice in each group. Animals were splenectomized following the injection.

Mice were bled at two weekly intervals for 3 months, and DNA was extracted from 100 μl sera. The DNA was subjected to PCR amplification. The DNA extraction and the PCR method applied are described in the legend of FIG. 3. Table 3 summarizes three experiments.

In mice implanted with HepG2-hIL6R cells (which have about one log higher expression of the receptor than HepG2 cells) subsequent to incubation with HBV in the presence of hIL6, HBV-DNA sequences could be detected in serum 13 days after transplantation, whereas HBV sequences were not detected in the sera of mice who underwent the same procedure without the presence of hIL6. Similar results were obtained in experiments using HepG2-PDI cells. These cells do not express the gp 80 binding protein subunit of the hIL6R on the cell membrane [S. Rose-John, et al., ibid.; M. Ehlers, et al., *The Journal of Immunology*, Vol. 153, p. 1744 (1994)], however, they do express the signal transduction gp 130 subunit of the receptor, which is essential for efficient internalization of hIL6 [E. Dittrich, et al., *The Journal of Biological Chemistry*, Vol. 269, pp. 10914–19020 (1994)].

In experiments of the same design, using HepG2 cells in the presence and also in the absence of hIL6, HBV sequences could be detected in a number of murine sera. These results are similar to those previously reported by Petit, et al. [R. Bchini, et al., ibid.], showing a low reproducibility in which only three sera supported HBV infection of HepG2 cells in-vitro, out of a total of 55 different serum samples taken from HBV DNA-positive patients. The HepG2-hIL6 cell line, which produces hIL6, generated HBV sequences in mice sera following incubation with the virus, with or without external supplementation of hIL6.

When the liver fragment was incubated ex-vivo with HBV-DNA positive sera in the presence of commercially available human polyclonal anti-HBs viral neutralizing antibodies (HBIG, Hepatect®, Biotest Pharma GmbH, Dreieich, Germany), HBV-DNA was observed at day 11 following transplantation only in 48% (10/21) of mice, as compared to 78% (14/18) of the untreated mice group (Table 4).

TABLE 4

Inhibition of infection-effect of anti-HBs antibodies effect on HBV-DNA levels in sera of chimeric mice transplanted with human liver fragments infected ex vivo with HBV

| Treatment Group | Mice Positive for HBV-DNA (%) |
|---|---|
| Untreated | 14/18 (78) |
| HBIG Treatment | 10/21 (48) |

Method:
For antibody treatment, HBV-DNA positive serum (0.5 ml) was incubated with 100 IU of HBIG for 2 hours at 25° C. Human liver fragments were then added to the untreated or HBIG treated HBV-DNA positive serum, according to the same protocol as described above, followed by implantation under the kidney capsule of the chimeric animal. Mice sera were analyzed for the presence of HBV-DNA sequences 11 days after transplantation.

Figure 2:
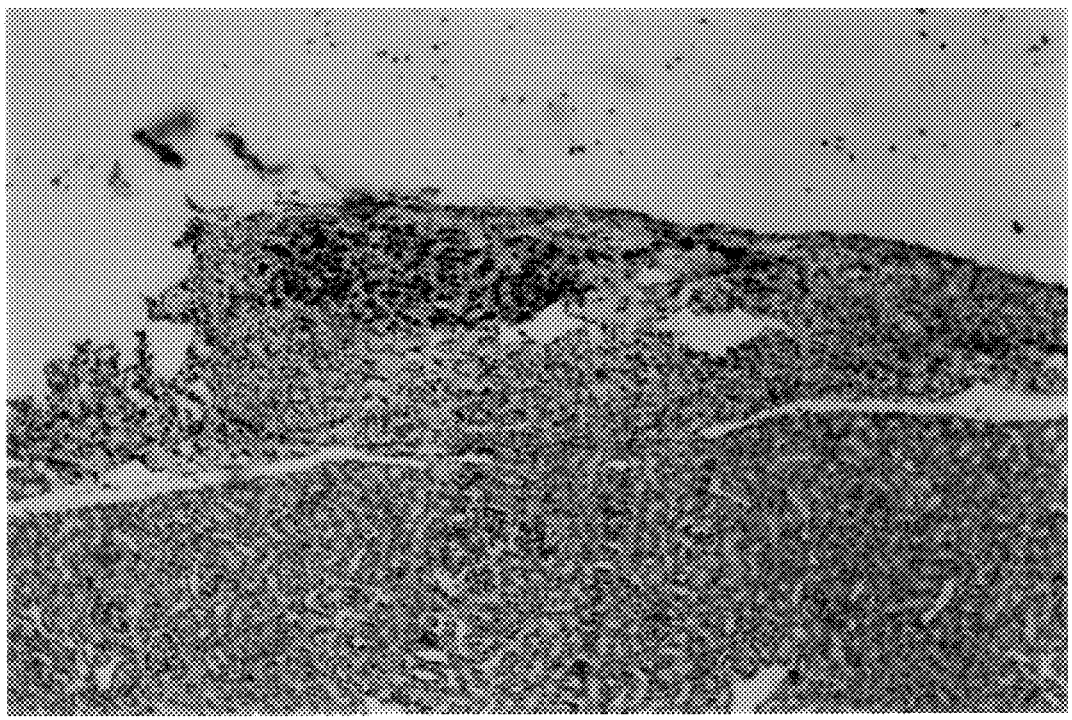
FIG. 2 illustrates a pre-infected liver fragment from a HBV DNA-positive patient, one month after sub-capsular implantation in a SCID>BNX chimeric mouse, stained for HbsAg.

Referring again to the figures, FIG. 2 shows pre-infected liver fragment from a HBV DNA-positive patient, one month after sub-capsular implantation in a SCID>BNX chimeric mouse, stained for HBsAg.

Figure 3C:
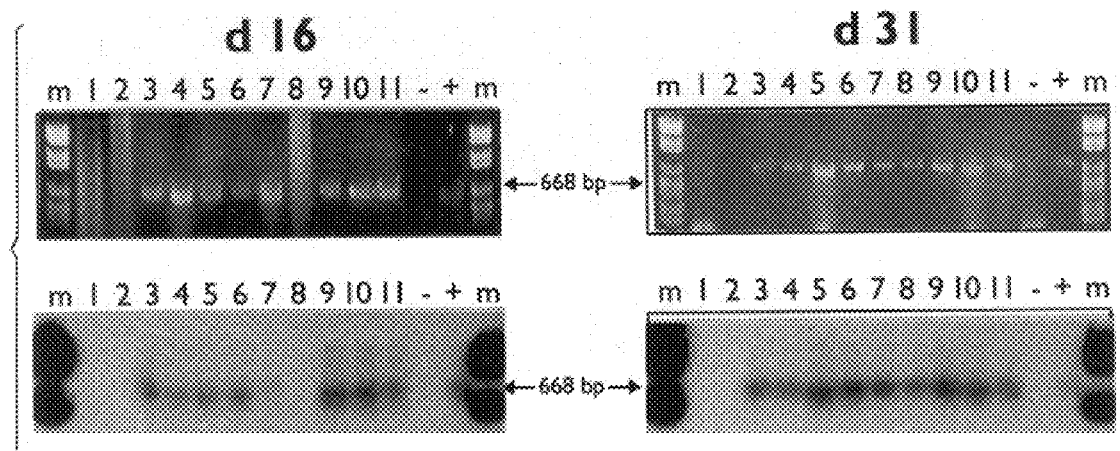
Figure 3D:
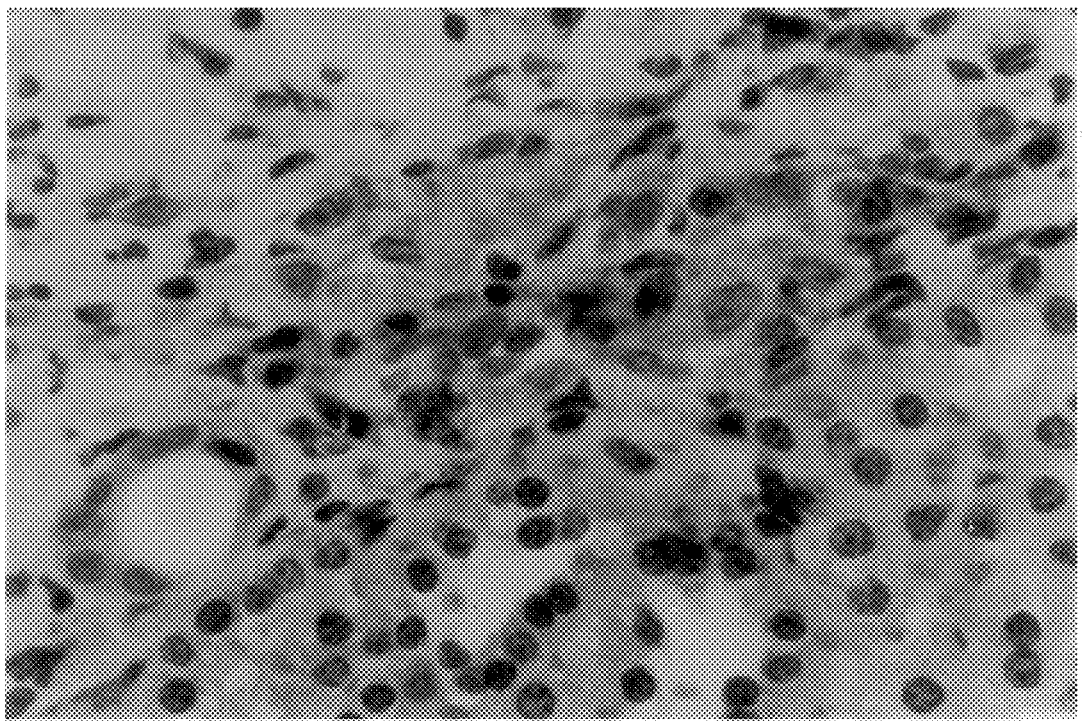

From FIGS. 3a–c it can be seen that hIL6 mediates HBV viremia in SCID>BNX chimeric mice transplanted with human tissue. PCR amplification products of HBV pre-core/core region following DNA extraction from sera of mice, 16 and 31 days after sub-capsular kidney transplantation of normal human liver fragments. The human liver fragments were incubated ex-vivo prior to transplantation with human HBV positive serum (FIG. 3a); HBV serum and hIL6 simultaneously (FIG. 3b), or preincubated with hIL6 and later with HBV sera (FIG. 3c). In each of FIGS. 3a to 3c, the upper panel is an EtBr staining and the lower panel is an $^{32}$p HBV linear insert hybridization result of the same gel. The molecular marker size (m) is indicated by an arrow; numbers at the head of each panel indicate mice identification numbers; + for positive serum control and − for negative serum control.

FIG. 3d shows HBsAg staining of an ex-vivo HBV incubation of a normal liver fragment with hIL6, one month following implantation under the kidney capsule of SCID>BNX mice.

Sera from HBV-positive patients, containing approximately 10$^8$ virions/ml, were used for infection. Small fragments of normal human liver were incubated with 400 μl sera in 1 ml DMEM supplemented with 2 μg/ml polybrene in the absence (group A) or presence (group B) of hIL6 (500 ng/ml) incubated for 2–4 h at 37° C. In group C, the liver fragments were treated with hIL6 for 2 h at 37° C. before the addition of HBV-positive sera and polybrene. After incubation, 4–5 ml polybrene DMEM were added and the liver fragments were transplanted under the kidney capsule to groups A, B and C of SCID>BNX chimeric mice (10, 19 and 11 mice, respectively). At 2 weekly intervals for 4 months, blood was collected retrobulbarily from each mouse. 100 μl of serum samples were treated with 0.5 mg/ml proteinase K in 10 mM EDTA and 0.25% SDS for 2 h at 55° C. or overnight at 37° C., extracted twice with phenol, once with phenol-$CHCl_3$, and once with $CHCl_3$. DNA was precipitated with ethanol, using 0.5M NaCl and a DNA microcarrier. DNA was dissolved in 30 μl Tris-EDTA, pH 8.0, and was subjected to PCR amplification.

The 50 μl PCR reaction volume contained 10 pmole of each oligonucleotide primer in reaction buffer (10 mM Tris-HCl, pH 8.3, 50 mM KCl, 2.0 mM $MgCl_2$, 0.01 % (w/v) gelatin, 250 μM of dATP, dGTP, dCTP, dTTP and 0.5 u of Taq polymerase. The reaction mixtures were overlaid with 30 μl of mineral oil. PCR cycles included 94° C. for 1 min., 55° C. for 1 min. and 72° C. for 3 min., 35 repeated cycles. 10 μl of reaction mixture was analyzed on a 2% agarose gel. Oligonucleotides used for the pre-core/core amplification were:

oligo 1, sense (nt 1778 to 1806):
5'GGA-GGC-TGT-AGG-CAT-AAA-TTG-GTC-TGC-GC-3'.

oligo 2, antisense (nt 2446 to 2408):
5'CCC-GAG-ATT-GAG-ATC-TTC-TGC-GAC-GCG-GCG-ATT-GAG-ACC-3'.

Sequence originated from adw subtype; nt numbering starts from EcoRI site. The expected size of the PCR DNA product is 668-bp.

The PCR samples were electrophoresed on 2% agarose gel and transferred to a nylon membrane (Biodynea), hybridized with a nick-translated probe. The autoradiogram was exposed with intensifying screens at −70° C. for 7 hours. In order to confirm the PCR results, the mice serum samples were also subjected to PCR amplification with primers spanning the envelope gene region, showing the same results (data not shown).

Reproducible results were obtained from four similar experiments, while there were 10–20 mice in each group.

The Effect of hIL-6 and hyper-IL-6 on HBV Infection of Human Mononuclear Cells

Human mononuclear cells are permissive for HBV infection. Lymphocytes have been shown to support HBV infection and also to harbor HBV integrated sequences [B.E. Korba, et al., *J. Virol.*, vol. 58, pp. 1–8 (1986); T. Laskus, et al, *J. Gen. Virol.*, vol. 78, pp. 649–653 (1997); T. Laskus, et al., *J. Virol.*, vol. 73, pp. 1235–1238 (1999)]. Lymphocytes also have been shown to express the IL-6 α and β receptors [M. Peters et al., *Blood*, vol. 92, pp. 3495–3504 (1998)]. The experiments set forth herein demonstrate that in the presence of hIL-6, the HBV infection of the mononuclear cells is enhanced; and that this infection is suppressed by the chimeric protein named Hyper-IL-6, which is generated by the fusion of hIL-6 to a soluble hIL-6 receptor (sIL-6Rα, gp80).

Method:

Long term human mononuclear culture: Human blood was withdrawn in $Li^{++}$-heparin collecting tubes from healthy donors. Serum samples from these donors were assessed for HBV serological and virological markers including HBV-DNA by PCR, as well as for HCV markers. All samples used in the experiments described were found negative for these viral markers including anti-HBc antibodies. Mononuclear cells were separated from 20–40 ml of blood by Ficoll-Hypaque sedimentation gradient, centrifuged at 800 g for 35 min at 20° C. Cells were collected and washed two times with RPMI 1640 medium containing 10% FCS, glutamine and antibiotics (penicillin and streptomycin). Cells were used for infection experiment, in part from fresh separation samples and in part from frozen samples stored in liquid nitrogen. Cells were cultured in the same separation medium and additives, containing 2 mg/ml of phytohemagglutinin (PHA), 20 U/ml of human IL-2, at 37° C. with 5% $CO_2$. After three days, mononuclear cells were infected with HBV sera, as will be described later. Following infection, the culture medium was supplemented with PHA and IL-2 every three-culture days. Cells were kept in culture for 21 days and over, under these conditions.

HBV infection protocol human mononuclear cells: Human sera were screened for the presence of HBV DNA sequences. Positive sera were analyzed quantitatively for viral particle concentration, as described by A. Klein, et al., *J. Clin. Microb.*, vol.35, pp. 1 897–1899 (1997). Sera containing over $10^8$ particles per ml were selected for infection experiments. For each infection experiment between $5 \times 10^6$ to $10^7$ PMNC were used. The infection experiments included the following groups: Group 1—Cells were incubated with HBV without the addition of hIL-6 in the presence of polybrene 2mg/ml, for 90 min at 37° C., in a 5% $CO_2$ shaking incubator, in a total volume of 1.5 to 2 ml. Group 2—Cells were incubated with 1 ml of HBV positive serum, in the presence of hIL-6 (500 ng/ml) and polybrene 2 mg/ml, for 90 min at 37° C., in a 5% $CO_2$ shaking incubator, in a total volume of 1.5 to 2 ml. Group 3—Cells were incubated with 1 ml of HBV positive serum, in the presence of the cytokine hyper-IL-6 (HIL-6), 1.5 mg/ml, and polybrene 2 mg/ml, for 90 min at 37° C., in a 5% $CO_2$ shaking incubator, in a total volume of 1.5 to 2 ml. The preparation of the cytokine hyper-IL-6 (HIL-6) is described in M. Fischer, et al., *Nat. Biotechnol.*, vol. 15, pp. 142–145 (1997); T. Rakemann et al., *J. Biol. Chem.*, vol. 274, pp. 1257–1266 (1999); P. Schirmacher, et al., *Am. J. Pathol.*, vol. 153, pp. 639–648 (1998). Following incubation of the viral-hIL-6 or viral HIL-6 mixtures, the cells were intensively washed three times with F-12 medium. The cells were continuously incubated in RPMI medium supplemented with 10 % FCS, PHA and hIL-2 as described above. Cells were harvested for HBV DNA extraction every three days up to day 21 following infection.

Results:

Incubation of HBV with human mononuclear cells resulted in the generation of relaxed circular ("RC") HBV DNA from day 4 post infection. The highest level of HBV DNA was detected at day 7 and decreased thereafter, as shown for both RC and covalently closed circular ("CCC") DNA species. In other experiments, HBV DNA, RC as well as CCC, were detected up to 21 days following infection (data not shown).

Figure 10:
FIG. 10 shows that HIL-6 inhibits HBV infection of human lymphocytes.

When the virus was incubated with hIL-6, HBV RC DNA was detected earlier and the level of HBV CCC DNA was higher (FIG. 10). In the in vitro infection assay used, HbsAg were not detected in the human mononuclear cells tested, a result similar to previous reported studies assessing HBV replication in mononuclear hematopoietic cells from HBV DNA positive patients [B.E. Korba, et al., *J. Virol.*, vol. 58, pp. 1–8 (1986); T. Laskus, et al., *J. Gen. Virol.*, vol. 78, pp. 649–653 (1997); T. Laskus, et al., *J. Virol.*, vol. 73, pp. 1235–1238 (1999)]. The supplementation of hIL-6 to the infection process facilitated the infection of lymphocytes in vitro, enabling the detection of HBV DNA earlier and possibly to a higher level.

When human mononuclear cells were incubated with HBV in the presence of hyper-hIL-6, RC and CCC HBV DNA viral species were reduced to undetectable levels. The morphology of the HBV infected and non-infected human mononuclear, cells, as well as their number, was identical at each time point for all three groups.

The Effect of hIL-6 and hyper-IL-6 on HBV Infection of Human Carcinoma Cell Line HuH7

The experiments set forth herein demonstrate that in the presence of hIL6, the HBV infection of the human carcinoma cell line HuH7 is enhanced. The experiments further show that HBV infection is suppressed by the chimeric protein named Hyper-IL-6, generated by the fusion of hIL-6 to a soluble hIL-6 receptor (sIL-6R, gp80).

Method:

HBV infection protocol of human hepatocellular carcinoma cell line HuH7: Human sera were screened for the presence of HBV DNA sequences. Positive sera were analyzed quantitatively for viral particle concentration, as described by A. Klein, *J. Clin. Microb.*, vol. 35, pp. 1897–1899 (1977). Sera containing over 108 particles per ml were selected for infection experiments. The infection experiments included the following groups: Group 1—Cells were incubated with HBV without the addition of hIL-6 in the presence of polybrene 2 mg/ml, for 90 min at 37° C., in a 5% $CO_2$ shaking incubator, in a total volume of 1.5 to 2 ml. Group 2—Cells were incubated with 1 ml of HBV positive serum, in the presence of hIL-6 (500 ng/ml) and polybrene 2 mg/ml, for 90 min at 37° C., in a 5% $CO_2$ incubator, in a total volume of 1.5 to 2 ml. Group 3—Cells were incubated with 1 ml of HBV positive serum, in the presence of the cytokine hyper-IL-6 (HIL-6), 1.5 mg/ml, and polybrene 2 mg/ml, for 90 min at 37° C., in a 5% $CO_2$ shaking incubator, in a total volume of 1.5 to 2 ml. The preparation of the cytokine hyper-IL-6 (HIL-6) is described in M. Fischer, et al., *Nat. Biotechnol.*, vol. 15, pp. 142–145 (1997); T. Rakemann et al., *J. Biol. Chem.*, vol. 274, pp. 1257–1266 (1999); P. Schirmacher et al., *Am. J. Pathol.*, vol. 153, pp. 639–648 (1998). Following incubation of the viral - hIL-6 or viral HIL-6 mixtures, the cells were intensively washed three times with medium. The cell were continuously incubated in DMEM medium supplemented with 10% FCS. Cells were harvested for HBV DNA extraction every three days up to day 21 following infection.

Figure 11:
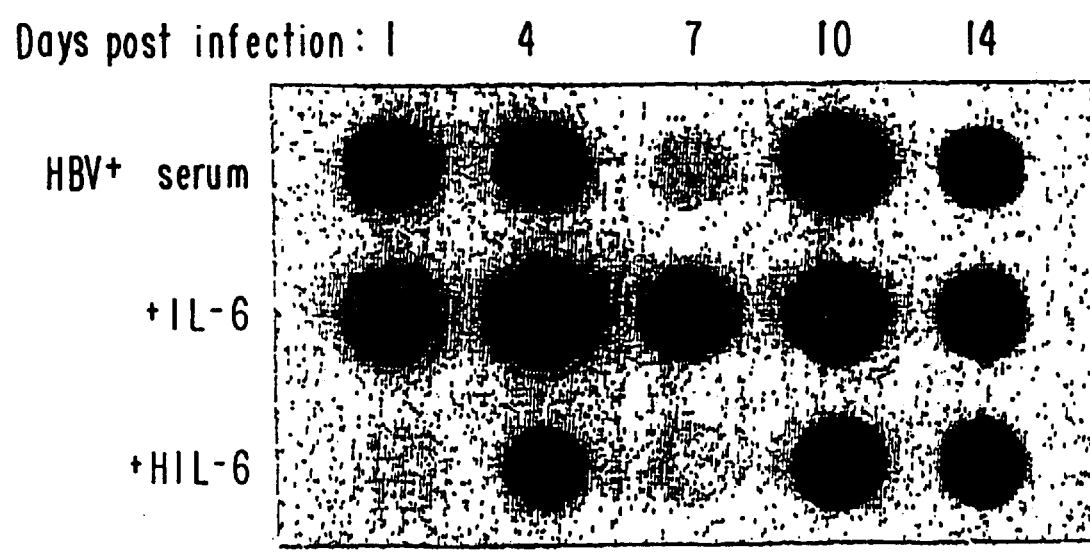
FIG. 11 shows that HIL-6 inhibits HBV infection of HuH7 cells.

Results:

Incubation of HBV with HuH7 cells resulted in the generation of RC HBV DNA from day 4 post infection. The highest level of HBV DNA was detected at days 7 to 14 and decreased thereafter, as shown for RC DNA species as shown in FIG. 11. However, when cells were incubated with HBV in the presence of hyper-hIL-6, HBV DNA was reduced to low levels. The morphology of the HBV infected and non-infected cells, as well as their number, was identical at each time point for all three groups.

With specific reference now to the examples and figures in detail, it is stressed that the particulars described and shown are by way of example and for purposes of illustrative discussion of the preferred embodiments of the present invention only, and are presented in the cause of providing what is believed to be the most useful and readily understood description of the principles and conceptual aspects of the invention. In this context, it is to be noted that only subject matter embraced in the scope of the claims appended hereto, whether in the manner defined in the claims or in a manner similar thereto and involving the main features, as defined in the claims, is intended to be included in the scope of the present invention. Furthermore, the proposed mechanisms of action set forth herein are for discussion purposes only and are not meant to limit the invention or the appended claims in any way.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

---

What is claimed is:

1. A method of inhibiting the infection of hepatocytes by HBV, comprising administering to a human patient a soluble active agent which inhibits the interaction between human interleukin 6 (hIL6) and hepatocytes, and thereby inhibits the activation of gp130 and the internalization of HBV into the hepatocytes, wherein the soluble active agent is selected from the group consisting of glycoprotein 80 (gp80) or a portion thereof, said portion spanning gp80 amino acids 113–323 and having receptor sites that interact with hIL6 and competitively inhibit the interaction between hIL6 and hepatocytes, glycoprotein 130 (gp130) or a portion thereof, said portion including amino acids 1–94 and 141–230, having receptor sites that interact with hIL6 and competitively inhibit the interaction between hIL6 and hepatocytes, hIL6 peptide LYS41-ALA56, hIL6 peptide GLY77-GLU95, hIL6 peptide GLN153-HIS165, a combined β1 and β2 hIL6 mutant (mhIL6β1+β2), mhIL6β1+β2 substituted with phe 171 to leu and ser 177 to arg, and mixtures of any of the foregoing.

2. The method of claim 1, wherein the soluble active agent comprises glycoprotein 80 (gp80) or a portion thereof having receptor sites that interact with hIL6 and competitively inhibit the interaction between hIL6 and hepatocytes.

3. The method of claim 1, wherein the soluble active agent comprises gp80.

4. The method of claim 1, wherein the soluble active agent comprises glycoprotein 130 (gp130) or a portion thereof having receptor sites that interact with hIL6 and competitively inhibit the interaction between hIL6 and hepatocytes.

5. The method of claim 1, wherein the soluble active agent comprises gp130.

6. The method of claim 1, wherein the soluble active agent consists essentially of a peptide comprising a hIL6 domain that interacts with hIL6Rα or hEL6β.

7. The method of claim 1, wherein the soluble active agent is selected from the group consisting of hIL6 peptide LYS41-ALA56, hIL6 peptide GLY77-GLU95, hIL6 peptide GLN153-HIS165, a combined β1 and β2 hIL6 mutant (mhIL6β1+β2), mhEL6β1+β2 substituted with phe 171 to leu and ser 177 to arg, and mixtures of any of the foregoing.

8. The method of claim 1, wherein the soluble active agent comprises hIL6 peptide LYS41-ALA56.

9. The method of claim 1, wherein the soluble active agent comprises hIL6 peptide GLY77-GLU95.

10. The method of claim 1, wherein the soluble active agent comprises hIL6 peptide GLN153-HIS165.

11. The method of claim 1, wherein the soluble active agent comprises a combined β1 and β2 hIL6 mutant (mhIL6β1+β2).

12. The method of claim 1, wherein the soluble active agent comprises mhIL6β1+β2 substituted with phe 171 to leu and ser 177 to arg.

13. The method of claim 1, wherein the soluble active agent disrupts the hIL6/hIL6Rα complex with hIL6Rβ.

14. The method of claim 1, wherein the soluble active agent disrupts the binding of hIL6 to hIL6Rα.

15. The method of claim 1, wherein the soluble active agent comprises hIL6 conjugated with an anti-viral agent, wherein the antiviral agent is glycoprotein 80 or a portion thereof having receptor sites that interact with hIL6 and competitively inhibit the interaction between hL6 and hepatocytes.

16. The method of claim 15, wherein the soluble active agent is Hyper-IL-6.

17. A method of the treatment of infection of hepatocytes with HBV, comprising administering to a human patient a soluble active agent which inhibits the interaction between human interleukin 6 (hIL6) and hepatocytes, wherein the soluble active agent is selected from the group consisting of glycoprotein 80 (gp80) or a portion thereof, said portion spanning gp80 amino acids 11 3–323 and having receptor sites that interact with hIL6 and competitively inhibit the interaction between hIL6 and hepatocytes, glycoprotein 130 (gp130) or a portion thereof, said portion including amino acids 1–94 and 141–230, having receptor sites that interact with hIL6 and competitively inhibit the interaction between hIL6 and hepatocytes, hIL6 peptide LYS41-ALA56, hIL6 peptide GLY77-GLU95, hIL6 peptide GLNI 53-HIS165, a combined β1 and β2 hIL6 mutant (mhIL6β1+β2), mhIL6β1+β2substituted with phe 171 to leu and ser 177 to arg, hyper-IL-6, and mixtures of any of the foregoing.

18. The method of claim 17, wherein the soluble active agent is selected from the group consisting of glycoprotein 80 (gp80) or a portion thereof having receptor sites that interact with hIL6 and competitively inhibit the interaction between hIL6 and hepatocytes, glycoprotein 130 (gp130) or a portion thereof having receptor sites that interact with hIL6 and competitively inhibit the interaction between hIL6 and hepatocytes, a peptide from the hIL6 domain that interacts with hIL6Rα or hIL6β, hIL6 peptide LYS41-ALA56, hIL6 peptide GLY77-GLU95, hIL6 peptide GLN153-HIS165, a combined β1 and β2 hIL6 mutant (mhIL6β1+β2), mhIL6β1+β2 substituted with phe 171 to leu and ser 177 to arg, a soluble agent which disrupts the hIL6/hIL6Rα complex with hIL6Rβ, and a soluble agent which disrupts the binding of hIL6 to hIL6Rα.

19. The method of claim 17, wherein the soluble active agent comprises glycoprotein 80 (gp80) or a portion thereof having receptor sites that interact with hIL6 and competitively inhibit the interaction between hIL6 and hepatocvtes.

20. The method of claim 17, wherein the soluble active agent is selected from the group consisting of hIL6 peptide LYS41-ALA56, hIL6 peptide GLY77-GLU95, hIL6 peptide GLN153-HIS165, a combined β1 and β2 hIL6 mutant (mhIL6β1+β2), mhIL6β1+β2 substituted with phe 171 to leu and ser 177 to arg, and mixtures of any of the foregoing.

21. The method of claim 17, wherein the soluble active agent is hyper-IL-6.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1128 base pairs
      (B) TYPE: nucleic acid
      (C) STRANDEDNESS: single
      (D) TOPOLOGY: unknown (xi) SEQUENCE DESCRIPTION: SEQ ID NO:1:

| | | | | | |
|---|---|---|---|---|---|
| ATTCTGCCCT | CGAGCCCACC | GGGAACGAAA | GAGAAGCTCT | ATCTCCCCTC | 50 |
| CAGGAGCCCA | GCTATGAACT | CCTTCTCCAC | AAGCGCCTTC | GGTCCAGTTG | 100 |
| CCTTCTCCCT | GGGGCTGCTC | CTGGTGTTGC | CTGCTGCCTT | CCCTGCCCCA | 150 |
| GTACCCCCAG | GAGAAGATTC | CAAAGATGTA | GCCGCCCAC | ACAGACAGCC | 200 |

-continued

| | |
|---|---|
| ACTCACCTCT TCAGAACGAA TTGACAAACA AATTCGGTAC ATCCTCGACG | 250 |
| GCATCTCAGC CCTGAGAAAG GAGACATGTA ACAAGAGTAA CATGTGTGAA | 300 |
| AGCAGCAAAG AGGCACTGGC AGAAAACAAC CTGAACCTTC CAAAGATGGC | 350 |
| TGAAAAAGAT GGATGCTTCC AATCTGGATT CAATGAGGAG ACTTGCCTGG | 400 |
| TGAAAATCAT CACTGGTCTT TTGGAGTTTG AGGTATACCT AGAGTACCTC | 450 |
| CAGAACAGAT TTGAGAGTAG TGAGGAACAA GCCAGAGCTG TCCAGATGAG | 500 |
| TACAAAAGTC CTGATCCAGT TCCTGCAGAA AAAGGCAAAG AATCTAGATG | 550 |
| CAATAACCAC CCCTGACCCA ACCACAAATG CCAGCCTGCT GACGAAGCTG | 600 |
| CAGGCACAGA ACCAGTGGCT GCAGGACATG ACAACTCATC TCATTCTGCG | 650 |
| CAGCTTTAAG GAGTTCCTGC AGTCCAGCCT GAGGGCTCTT CGGCAAATGT | 700 |
| AGCATGGGCA CCTCAGATTG TTGTTGTTAA TGGGCATTCC TTCTTCTGGT | 750 |
| CAGAAACCTG TCCACTGGGC ACAGAACTTA TGTTGTTCTC TATGGAGAAC | 800 |
| TAAAAGTATG AGCGTTAGGA CACTATTTTA ATTATTTTA ATTTATTAAT | 850 |
| ATTTAAATAT GTGAAGCTGA GTTAATTTAT GTAAGTCATA TTTTATATTT | 900 |
| TTAAGAAGTA CCACTTGAAA CATTTTATGT ATTAGTTTTG AAATAATAAT | 950 |
| GGAAAGTGGC TATGCAGTTT GAATATCCTT TGTTTCAGAG CCAGATCATT | 1000 |
| TCTTGGAAAG TGTAGGCTTA CCTCAAATAA ATGGCTAACT TTATACATAT | 1050 |
| TTTTAAAGAA ATATTTATAT TGTATTTATA TAATGTATAA ATGGTTTTTA | 1100 |
| TACCAATAAA TGGCATTTTA AAAAATTC | 1128 |

(2) INFORMATION FOR SEQ ID NO:2:

(i) SEQUENCE CHARACTERISTICS:
        (A) LENGTH: 3319 base pairs
        (B) TYPE: nucleic acid
        (C) STRANDEDNESS: single
        (D) TOPOLOGY: unknown (xi) SEQUENCE DESCRIPTION: SEQ ID NO:2:

| | |
|---|---|
| GGCGGTCCCC TGTTCTCCCC GCTCAGGTGC GGCGCTGTGG CAGGAAGCCA | 50 |
| CCCCCTCGGT CGGCCGGTGC GCGGGGCTGT TGCGCCATCC GCTCCGGCTT | 100 |
| TCGTAACCGC ACCCTGGGAC GGCCCAGAGA CGCTCCAGCG CGAGTTCCTC | 150 |
| AAATGTTTTC CTGCGTTGCC AGGACCGTCC GCCGCTCTGA GTCATGTGCG | 200 |
| AGTGGGAAGT CGCACTGACA CTGAGCCGGG CCAGAGGGAG AGGAGCCGAG | 250 |
| CGCGGCGCGG GGCCGAGGGA CTCGCAGTGT GTGTAGAGAG CCGGGCTCCT | 300 |
| GCGGATGGGG GCTGCCCCCG GGGCCTGAGC CCGCCTGCCC GCCCACCGCC | 350 |
| CCGCCCCGCC CCTGCCACCC CTGCCGCCCG GTTCCCATTA GCCTGTCCGC | 400 |
| CTCTGCGGGA CCATGGAGTG GTAGCCGAGG AGGAAGCATG CTGGCCGTCG | 450 |
| GCTGCGCGCT GCTGGCTGCC CTGCTGGCCG CGCCGGGAGC GGCGCTGGCC | 500 |
| CCAAGGCGCT GCCCTGCGCA GGAGGTGGCA AGAGGCGTGC TGACCAGTCT | 550 |
| GCCAGGAGAC AGCGTGACTC TGACCTGCCC GGGGGTAGAG CCGGAAGACA | 600 |
| ATGCCACTGT TCACTGGGTG CTCAGGAAGC CGGCTGCAGG CTCCCACCCC | 650 |
| AGCAGATGGG CTGGCATGGG AAGGAGGCTG CTGCTGAGGT CGGTGCAGCT | 700 |
| CCACGACTCT GGAAACTATT CATGCTACCG GGCCGGCCGC CCAGCTGGGA | 750 |

-continued

| | |
|---|---|
| CTGTGCACTT GCTGGTGGAT GTTCCCCCCG AGGAGCCCCA GCTCTCCTGC | 800 |
| TTCCGGAAGA GCCCCCTCAG CAATGTTGTT TGTGAGTGGG GTCCTCGGAG | 850 |
| CACCCCATCC CTGACGACAA AGGCTGTGCT CTTGGTGAGG AAGTTTCAGA | 900 |
| ACAGTCCGGC CGAAGACTTC CAGGAGCCGT GCCAGTATTC CCAGGAGTCC | 950 |
| CAGAAGTTCT CCTGCCAGTT AGCAGTCCCG GAGGGAGACA GCTCTTTCTA | 1000 |
| CATAGTGTCC ATGTGCGTCG CCAGTAGTGT CGGGAGCAAG TTCAGCAAAA | 1050 |
| CTCAAACCTT TCAGGGTTGT GGAATCTTGC AGCCTGATCC GCCTGCCAAC | 1100 |
| ATCACAGTCA CTGCCGTGGC CAGAAACCCC CGCTGGCTCA GTGTCACCTG | 1150 |
| GCAAGACCCC CACTCCTGGA ACTCATCTTT CTACAGACTA CGGTTTGAGC | 1200 |
| TCAGATATCG GGCTGAACGG TCAAAGACAT TCACAACATG GATGGTCAAG | 1250 |
| GACCTCCAGC ATCACTGTGT CATCCACGAC GCCTGGAGCG GCCTGAGGCA | 1300 |
| CGTGGTGCAG CTTCGTGCCC AGGAGGAGTT CGGGCAAGGC GAGTGGAGCG | 1350 |
| AGTGGAGCCC GGAGGCCATG GGCACGCCTT GGACAGAATC CAGGAGTCCT | 1400 |
| CCAGCTGAGA ACGAGGTGTC CACCCCCATG CAGGCACTTA CTACTAATAA | 1450 |
| AGACGATGAT AATATTCTCT TCAGAGATTC TGCAAATGCG ACAAGCCTCC | 1500 |
| CAGTGCAAGA TTCTTCTTCA GTACCACTGC CCACATTCCT GGTTGCTGGA | 1550 |
| GGGAGCCTGG CCTTCGGAAC GCTCCTCTGC ATTGCCATTG TTCTGAGGTT | 1600 |
| CAAGAAGACG TGGAAGCTGC GGGCTCTGAA GGAAGGCAAG ACAAGCATGC | 1650 |
| ATCCGCCGTA CTCTTTGGGG CAGCTGGTCC CGGAGAGGCC TCGACCCACC | 1700 |
| CCAGTGCTTG TTCCTCTCAT CTCCCCACCG GTGTCCCCCA GCAGCCTGGG | 1750 |
| GTCTGACAAT ACCTCGAGCC ACAACCGACC AGATGCCAGG GACCCACGGA | 1800 |
| GCCCTTATGA CATCAGCAAT ACAGACTACT TCTTCCCCAG ATAGCTGGCT | 1850 |
| GGGTGGCACC AGCAGCCTGG ACCCTGTGGA TGACAAAACA CAAACGGGCT | 1900 |
| CAGCAAAAGA TGCTTCTCAC TGCCATGCCA GCTTATCTCA GGGGTGTGCG | 1950 |
| GCCTTTGGCT TCACGGAAGA GCCTTGCGGA AGGTTCTACG CCAGGGGAAA | 2000 |
| ATCAGCCTGC TCCAGCTGTT CAGCTGGTTG AGGTTTCAAA CCTCCCTTTC | 2050 |
| CAAATGCCCA GCTTAAAGGG GTTAGAGTGA ACTTGGGCCA CTGTGAAGAG | 2100 |
| AACCATATCA AGACTCTTTG GACACTCACA CGGACACTCA AAAGCTGGGC | 2150 |
| AGGTTGGTGG GGGCCTCGGT GTGGAGAAGC GGCTGGCAGC CCACCCCTCA | 2200 |
| ACACCTCTGC ACAAGCTGCA CCCTCAGGCA GGTGGGATGA ATTTCCAGCC | 2250 |
| AAAGCCTCCT CCAGCCGCCA TGCTCCTGGC CCACTGCATC GTTTCATCTT | 2300 |
| CCAACTCAAA CTCTTAAAAC CCAAGTGCCC TTAGCAAATT CTGTTTTTCT | 2350 |
| AGGCCTGGGG ACGGCTTTTA CTTAAACGCC AAGGCCTGGG GGAAGAAGCT | 2400 |
| CTCTCCTCCC TTTCTTCCCT ACAGTTCAAA AACAGCTGAG GGTGAGTGGG | 2450 |
| TGAATAATAC AGTATGTCAG GGCCTGGTCG TTTTCAACAG AATTATAATT | 2500 |
| AGTTCCTCAT TAGCAGTTTT GCCTAAATGT GAATGATGAT CCTAGGCATT | 2550 |
| TGCTGAATAC AGAGGCAACT GCATTGGCTT TGGGTTGCAG GACCTCAGGT | 2600 |
| GAGAAGCAGA GGAAGGAGAG GAGAGGGGCA CAGGGTCTCT ACCATCCCCT | 2650 |
| GTAGAGTGGG AGCTGAGTGG GGGATCACAG CCTCTGAAAA CCAATGTTCT | 2700 |
| CTCTTCTCCA CCTCCCACAA AGGAGAGCTA GCAGCAGGGA GGGCTTCTGC | 2750 |

| | |
|---|---|
| CATTTCTGAG ATCAAAACGG TTTTACTGCA GCTTTGTTTG TTGTCAGCTG | 2800 |
| AACCTGGGTA ACTAGGGAAG ATAATATTAA GGAAGACAAT GTGAAAAGAA | 2850 |
| AAATGAGCCT GGCAAGAATG CGTTTAAACT TGGTTTTTAA AAAACTGCTG | 2900 |
| ACTGTTTTCT CTTGAGAGGG TGGAATATCC AATATTCGCT GTGTCAGCAT | 2950 |
| AGAAGTAACT TACTTAGGTG TGGGGGAAGC ACCATAACTT TGTTTAGCCC | 3000 |
| AAAACCAAGT CAAGTGAAAA AGGAGGAAGA GAAAAAATAT TTTCCTGCCA | 3050 |
| GGCATGGAGG CCCACGCACT TCGGGAGGTC GAGGCAGGAG GATCACTTGA | 3100 |
| GTCCAGAAGT TTGAGATCAG CCTGGGCAAT GTGATAAAAC CCCATCTCTA | 3150 |
| CAAAAAGCAT AAAAATTAGC CAAGTGTGGT AGAGTGTGCC TGAAGTCCCA | 3200 |
| GATACTTGGG GGGCTGAGGT GGGAGGATCT CTTGAGCCTG GGAGGTCAAG | 3250 |
| GCTGCAGTGA GCCGAGATTG CACCACTGCA CTCCAGCCTG GGGTGACAGA | 3300 |
| GCAAGTGAGA CCCTGTCTC | 3319 |

(2) INFORMATION FOR SEQ ID NO:3:

(i) SEQUENCE CHARACTERISTICS:
        (A) LENGTH: 1486 base pairs
        (B) TYPE: nucleic acid
        (C) STRANDEDNESS: single
        (D) TOPOLOGY: unknown (xi) SEQUENCE DESCRIPTION: SEQ ID NO:3:

| | |
|---|---|
| ATTAGCCTGT CCGCCTCTGC GGGACCATGG AGTGGTAGCC GAGGAGGAAG | 50 |
| CATGCTGGCC GTCGGCTGCG CGCTGCTGGC TGCCCTGCTG GCCGCGCCGG | 100 |
| GAGCGGCGCT GGCCCCAAGG CGCTGCCCTG CGCAGGAGGT GGCGAGAGGC | 150 |
| GTGCTGACCA GTCTGCCAGG AGACAGCGTG ACTCTGACCT GCCCGGGGGT | 200 |
| AGAGCCGGAA GACAATGCCA CTGTTCACTG GGTGCTCAGG AAGCCGGCTG | 250 |
| CAGGCTCCCA CCCCAGCAGA TGGGCTGGCA TGGGAAGGAG GCTGCTGCTG | 300 |
| AGGTCGGTGC AGCTCCACGA CTCTGGAAAC TATTCATGCT ACCGGGCCGG | 350 |
| CCGCCCAGCT GGGACTGTGC ACTTGCTGGT GGATGTTCCC CCCGAGGAGC | 400 |
| CCCAGCTCTC CTGCTTCCGG AAGAGCCCCC TCAGCAATGT TGTTTGTGAG | 450 |
| TGGGGTCCTC GGAGCACCCC ATCCCTGACG ACAAAGGCTG TGCTCTTGGT | 500 |
| GAGGAAGTTT CAGAACAGTC CGGCCGAAGA CTTCCAGGAG CCGTGCCAGT | 550 |
| ATTCCCAGGA GTCCCAGAAG TTCTCCTGCC AGTTAGCAGT CCCGGAGGGA | 600 |
| GACAGCTCTT TCTACATAGT GTCCATGTGC GTCGCCAGTA GTGTCGGGAG | 650 |
| CAAGTTCAGC AAAACTCAAA CCTTTCAGGG TTGTGGAATC TTGCAGCCTG | 700 |
| ATCCGCCTGC CAACATCACA GTCACTGCCG TGGCCAGAAA CCCCCGCTGG | 750 |
| CTCAGTGTCA CCTGGCAAGA CCCCCACTCC TGGAACTCAT CTTTCTACAG | 800 |
| ACTACGGTTT GAGCTCAGAT ATCGGGCTGA ACGGTCAAAG ACATTCACAA | 850 |
| CATGGATGGT CAAGGACCTC CAGCATCACT GTGTCATCCA CGACGCCTGG | 900 |
| AGCGGCCTGA GGCACGTGGT GCAGCTTCGT GCCCAGGAGG AGTTCGGGCA | 950 |
| AGGCGAGTGG AGCGAGTGGA GCCCGGAGGC CATGGGCACG CCTTGGACAG | 1000 |
| AATCCAGGAG TCCTCCAGCT GAGAACGAGG TGTCCACCCC CATGCAGGCA | 1050 |
| CTTACTACTA ATAAAGACGA TGATAATATT CTCTTCAGAG ATTCTGCAAA | 1100 |

| | |
|---|---|
| TGCGACAAGC CTCCCAGTGC AAGATTCTTC TTCAGTACCA CTGCCCACAT | 1150 |
| TCCTGGTTGC TGGAGGGAGC CTGGCCTTCG GAACGCTCCT CTGCATTGCC | 1200 |
| ATTGTTCTGA GGTTCAAGAA GACGTGGAAG CTGCGGGCTC TGAAGGAAGG | 1250 |
| CAAGACAAGC ATGCATCCGC CGTACTCTTT GGGGCAGCTG GTCCCGGAGA | 1300 |
| GGCCTCGACC CACCCCAGTG CTTGTTCCTC TCATCTCCCC ACCGGTGTCC | 1350 |
| CCCAGCAGCC TGGGGTCTGA CAATACCTCG AGCCACAACC GACCAGATGC | 1400 |
| CAGGGACCCA CGGAGCCCTT ATGACATCAG CAATACAGAC TACTTCTTCC | 1450 |
| CCAGATAGCT GGCTGGGTGG CACCAGCAGC CTGGAC | 1486 |

(2) INFORMATION FOR SEQ ID NO:4:

(i) SEQUENCE CHARACTERISTICS:
        (A) LENGTH: 3085 base pairs
        (B) TYPE: nucleic acid
        (C) STRANDEDNESS: single
        (D) TOPOLOGY: unknown (xi) SEQUENCE DESCRIPTION: SEQ ID NO: 4:

| | |
|---|---|
| GAGCAGCCAA AAGGCCCGCG GAGTCGCGCT GGGCCGCCCC GGCGCAGCTG | 50 |
| AACCGGGGGC CGCGCCTGCC AGGCCGACGG GTCTGGCCCA GCCTGGCGCC | 100 |
| AAGGGGTTCG TGCGCTGTGG AGACGCGGAG GGTCGAGGCG GCGCGGCCTG | 150 |
| AGTGAAACCC AATGGAAAAA GCATGACATT TAGAAGTAGA AGACTTAGCT | 200 |
| TCAAATCCCT ACTCCTTCAC TTACTAATTT TGTGATTTGG AAATATCCGC | 250 |
| GCAAGATGTT GACGTTGCAG ACTTGGGTAG TGCAAGCCTT GTTTATTTTC | 300 |
| CTCACCACTG AATCTACAGG TGAACTTCTA GATCCATGTG GTTATATCAG | 350 |
| TCCTGAATCT CCAGTTGTAC AACTTCATTC TAATTTCACT GCAGTTTGTG | 400 |
| TGCTAAAGGA AAAATGTATG GATTATTTTC ATGTAAATGC TAATTACATT | 450 |
| GTCTGGAAAA CAAACCATTT TACTATTCCT AAGGAGCAAT ATACTATCAT | 500 |
| AAACAGAACA GCATCCAGTG TCACCTTTAC AGATATAGCT TCATTAAATA | 550 |
| TTCAGCTCAC TTGCAACATT CTTACATTCG ACAGCTTGA ACAGAATGTT | 600 |
| TATGGAATCA CAATAATTTC AGGCTTGCCT CCAGAAAAAC CTAAAAATTT | 650 |
| GAGTTGCATT GTGAACGAGG GGAAGAAAAT GAGGTGTGAG TGGGATGGTG | 700 |
| GAAGGGAAAC ACACTTGGAG ACAAACTTCA CTTTAAAATC TGAATGGGCA | 750 |
| ACACACAAGT TTGCTGATTG CAAAGCAAAA CGTGACACCC CCACCTCATG | 800 |
| CACTGTTGAT TATTCTACTG TGTATTTTGT CAACATTGAA GTCTGGGTAG | 850 |
| AAGCAGAGAA TGCCCTTGGG AAGGTTACAT CAGATCATAT CAATTTTGAT | 900 |
| CCTGTATATA AAGTGAAGCC CAATCCGCCA CATAATTTAT CAGTGATCAA | 950 |
| CTCAGAGGAA CTGTCTAGTA TCTTAAAATT GACATGGACC AACCCAAGTA | 1000 |
| TTAAGAGTGT TATAATACTA AAATATAACA TTCAATATAG GACCAAAGAT | 1050 |
| GCCTCAACTT GGAGCCAGAT TCCTCCTGAA GACACAGCAT CCACCCGATC | 1100 |
| TTCATTCACT GTCCAAGACC TTAAACCTTT TACAGAATAT GTGTTAGGA | 1150 |
| TTCGCTGTAT GAAGGAAGAT GGTAAGGGAT ACTGGAGTGA CTGGAGTGAA | 1200 |
| GAAGCAAGTG GGATCACCTA TGAAGATAGA CCATCTAAAG CACCAAGTTT | 1250 |
| CTGGTATAAA ATAGATCCAT CCCATACTCA AGGCTACAGA ACTGTACAAC | 1300 |

```
TCGTGTGGAA GACATTGCCT CCTTTTGAAG CCAATGGAAA AATCTTGGAT        1350

TATGAAGTGA CTCTCACAAG ATGGAAATCA CATTTACAAA ATTACACAGT        1400

TAATGCCACA AAACTGACAG TAAATCTCAC AAATGATCGC TATCTAGCAA        1450

CCCTAACAGT AAGAAATCTT GTTGGCAAAT CAGATGCAGC TGTTTTAACT        1500

ATCCCTGCCT GTGACTTTCA AGCTACTCAC CCTGTAATGG ATCTTAAAGC        1550

ATTCCCCAAA GATAACATGC TTTGGGTGGA ATGGACTACT CCAAGGGAAT        1600

CTGTAAAGAA ATATATACTT GAGTGGTGTG TGTTATCAGA TAAAGCACCC        1650

TGTATCACAG ACTGGCAACA AGAAGATGGT ACCGTGCATC GCACCTATTT        1700

AAGAGGGAAC TTAGCAGAGA GCAAATGCTA TTTGATAACA GTTACTCCAG        1750

TATATGCTGA TGGACCAGGA AGCCCTGAAT CCATAAAGGC ATACCTTAAA        1800

CAAGCTCCAC CTTCCAAAGG ACCTACTGTT CGGACAAAAA AAGTAGGGAA        1850

AAACGAAGCT GTCTTAGAGT GGGACCAACT TCCTGTTGAT GTTCAGAATG        1900

GATTTATCAG AAATTATACT ATATTTTATA GAACCATCAT TGGAAATGAA        1950

ACTGCTGTGA ATGTGGATTC TTCCCACACA GAATATACAT TGTCCTCTTT        2000

GACTAGTGAC ACATTGTACA TGGTACGAAT GGCAGCATAC ACAGATGAAG        2050

GTGGGAAGGA TGGTCCAGAA TTCACTTTTA CTACCCCAAA GTTTGCTCAA        2100

GGAGAAATTG AAGCCATAGT CGTGCCTGTT TGCTTAGCAT TCCTATTGAC        2150

AACTCTTCTG GGAGTGCTGT TCTGCTTTAA TAAGCGAGAC CTAATTAAAA        2200

AACACATCTG GCCTAATGTT CCAGATCCTT CAAAGAGTCA TATTGCCCAG        2250

TGGTCACCTC ACACTCCTCC AAGGCACAAT TTTAATTCAA AAGATCAAAT        2300

GTATCCAGAT GGCAATTTCA CTGATGTAAG TGTTGTGGAA ATAGAAGCAA        2350

ATGACAAAAA GCCTTTTCCA GAAGATCTGA ATCATTGGA CCTGTTCAAA         2400

AAGGAAAAAA TTAATACTGA AGGACACAGC AGTGGTATTG GGGGTCTTC         2450

ATGCATGTCA TCTTCTAGGC AAGCATTTC TAGCAGTGAT GAAAATGAAT         2500

CTTCACAAAA CACTTCGAGC ACTGTCCAGT ATTCTACCGT GGTACACAGT        2550

GGCTACAGAC ACCAAGTTCC GTCAGTCCAA GTCTTCTCAA GATCCGAGTC        2600

TACCCAGCCC TTGTTAGATT CAGAGGAGCG GCCAGAAGAT CTACAATTAG        2650

TAGATCATGT AGATGGCGGT GATGGTATTT TGCCCAGGCA ACAGTACTTC        2700

AAACAGAACT GCAGTCAGCA TGAATCCAGT CCAGATATTT CACATTTGA         2750

AAGGTCAAAG CAAGTTTCAT CAGTCAATGA GGAAGATTTT GTTAGACTTA        2800

AACAGCAGAT TTCAGATCAT ATTTCACAAT CCTGTGGATC TGGGCAAATG        2850

AAAATGTTTC AGGAAGTTTC TGCAGCAGAT GCTTTTGGTC CAGGTACTGA        2900

GGACAAGTA GAAAGATTTG AAACAGTTGG CATGGAGGCT GCGACTGATG         2950

AAGGCATGCC TAAAAGTTAC TTACCACAGA CTGTACGGCA AGGCGGCTAC        3000

ATGCCTCAGT GAAGGACTAG TAGTTCCTGC TACAACTTCA GCAGTACCTA        3050

TAAAGTAAAG CTAAAATGAT TTTATCTGTG AATTC                        3085
```

(2) INFORMATION FOR SEQ ID NO:5:

(i) SEQUENCE CHARACTERISTICS:
        (A) LENGTH: 468 amino acids
        (B) TYPE: amino acid (D) TOPOLOGY: unknown (xi) SEQUENCE DESCRIPTION: SEQ ID NO: 5:

```
Met Leu Ala Val Gly Cys Ala Leu Leu Ala Ala Leu Leu Ala Ala Pro
              5                  10                  15
Gly Ala Ala Leu Ala Pro Arg Arg Cys Pro Ala Gln Glu Val Ala Arg
             20                  25                  30
Gly Val Leu Thr Ser Leu Pro Gly Asp Ser Val Thr Leu Thr Cys Pro
             35                  40                  45
Gly Val Glu Pro Glu Asp Asn Ala Thr Val His Trp Val Leu Arg Lys
 50                  55                  60
Pro Ala Gly Ser His Pro Ser Arg Trp Ala Gly Met Gly Arg Arg
 65                  70                  75                  80
Leu Leu Leu Arg Ser Val Gln Leu His Asp Ser Gly Asn Tyr Ser Cys
                 85                  90                  95
Tyr Arg Ala Gly Arg Pro Ala Gly Thr Val His Leu Leu Val Asp Val
                100                 105                 110
Pro Pro Glu Glu Pro Gln Leu Ser Cys Phe Arg Lys Ser Pro Leu Ser
            115                 120                 125
Asn Val Val Cys Glu Trp Gly Pro Arg Ser Thr Pro Ser Leu Thr Thr
130                 135                 140
Lys Ala Val Leu Leu Val Arg Lys Phe Gln Asn Ser Pro Ala Glu Asp
145                 150                 155                 160
Phe Gln Glu Pro Cys Gln Tyr Ser Gln Glu Ser Gln Lys Phe Ser Cys
                165                 170                 175
Gln Leu Ala Val Pro Glu Gly Asp Ser Ser Phe Tyr Ile Val Ser Met
            180                 185                 190
Cys Val Ala Ser Ser Val Gly Ser Lys Phe Ser Lys Thr Gln Thr Phe
            195                 200                 205
Gln Gly Cys Gly Ile Leu Gln Pro Asp Pro Ala Asn Ile Thr Val
            210                 215                 220
Thr Ala Val Ala Arg Asn Pro Arg Trp Leu Ser Val Thr Trp Gln Asp
225                 230                 235                 240
Pro His Ser Trp Asn Ser Ser Phe Tyr Arg Leu Arg Phe Glu Leu Arg
                245                 250                 255
Tyr Arg Ala Glu Arg Ser Lys Thr Phe Thr Thr Trp Met Val Lys Asp
            260                 265                 270
Leu Gln His His Cys Val Ile His Asp Ala Trp Ser Gly Leu Arg His
            275                 280                 285
Val Val Gln Leu Arg Ala Gln Glu Glu Phe Gly Gln Gly Glu Trp Ser
290                 295                 300
Glu Trp Ser Pro Glu Ala Met Gly Thr Pro Trp Thr Glu Ser Arg Ser
305                 310                 315                 320
Pro Pro Ala Glu Asn Glu Val Ser Thr Pro Met Gln Ala Leu Thr Thr
                325                 330                 335
Asn Lys Asp Asp Asp Asn Ile Leu Phe Arg Asp Ser Ala Asn Ala Thr
            340                 345                 350
Ser Leu Pro Val Gln Asp Ser Ser Val Pro Leu Pro Thr Phe Leu
            355                 360                 365
Val Ala Gly Gly Ser Leu Ala Phe Gly Thr Leu Leu Cys Ile Ala Ile
370                 375                 380
Val Leu Arg Phe Lys Lys Thr Trp Lys Leu Arg Ala Leu Lys Glu Gly
385                 390                 395                 400
```

```
Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
                420                 425                 430

Ser Pro Ser Ser Leu Gly Ser Asp Asn Thr Ser Ser His Asn Arg Pro
                435                 440                 445

Asp Ala Arg Asp Pro Arg Ser Pro Tyr Asp Ile Ser Asn Thr Asp Tyr
            450                 455                 460

Phe Phe Pro Arg
465
```

(2) INFORMATION FOR SEQ ID NO:6:

(i) SEQUENCE CHARACTERISTICS:
        (A) LENGTH: 212 amino acids
        (B) TYPE: amino acid
        (D) TOPOLOGY: unknown (xi) SEQUENCE DESCRIPTION: SEQ ID NO: 6:

```
Met Asn Ser Phe Ser Thr Ser Ala Phe Gly Pro Val Ala Phe Ser Leu
 1               5                  10                  15

Gly Leu Leu Val Leu Pro Ala Ala Phe Ala Pro Val Pro Pro
                20                  25                  30

Gly Glu Asp Ser Lys Asp Val Ala Ala Pro His Arg Gln Pro Leu Thr
                35                  40                  45

Ser Ser Glu Arg Ile Asp Lys Gln Ile Arg Tyr Ile Leu Asp Gly Ile
50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
                100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
                180                 185                 190

Leu Ile Leu Arg Ser Phe Lys Glu Phe Leu Gln Ser Ser Leu Arg Ala
            195                 200                 205

Leu Arg Gln Met
        210
```

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (xi) SEQUENCE DESCRIPTION: SEQ ID NO:7:

GGAGGCTGTA GGCATAAATT GGTCTGCGC        29

(2) INFORMATION FOR SEQ ID NO:8:

(i) SEQUENCE CHARACTERISTICS:
        (A) LENGTH: 39 base pairs
        (B) TYPE: nucleic acid
        (C) STRANDEDNESS: single
        (D) TOPOLOGY: unknown (xi) SEQUENCE DESCRIPTION: SEQ ID NO:8:

CCCGAGATTG AGATCTTCTG CGACGCGGCG ATTGAGACC                          39

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: unknown (ii) SEQUENCE DESCRIPTION: SEQ ID NO:9:

CGGGATCCAT GGGAGGTTGG TCATC                                         25

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: unknown (xi) SEQUENCE DESCRIPTION: SEQ ID NO:10:

GGAATTCCAC TGCATGGC                                                 18